United States Patent
Zemel et al.

(10) Patent No.: US 9,713,609 B2
(45) Date of Patent: *Jul. 25, 2017

(54) COMPOSITIONS, METHODS, AND KITS FOR REGULATING ENERGY METABOLISM

(71) Applicant: NuSirt Sciences, Inc., Nashville, TN (US)

(72) Inventors: Michael Zemel, Knoxville, TN (US); E. Douglas Grindstaff, II, Nashville, TN (US)

(73) Assignee: NuSirt Sciences, Inc., Nashville, TN (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/206,183

(22) Filed: Jul. 8, 2016

(65) Prior Publication Data

US 2017/0000777 A1 Jan. 5, 2017

Related U.S. Application Data

(63) Continuation of application No. 14/927,228, filed on Oct. 29, 2015, now Pat. No. 9,408,410, which is a
(Continued)

(51) Int. Cl.
*A61K 31/4415* (2006.01)
*A23L 33/175* (2016.01)
(Continued)

(52) U.S. Cl.
CPC .......... *A61K 31/4415* (2013.01); *A23L 33/15* (2016.08); *A23L 33/175* (2016.08);
(Continued)

(58) Field of Classification Search
CPC .............. A61K 31/4415; A61K 31/194; A61K 31/191; A61K 31/198; A61K 31/155; A23L 33/175; A23L 33/15; A23V 2002/00
See application file for complete search history.

(56) References Cited

U.S. PATENT DOCUMENTS 3,810,994 A 5/1974 Wiegand
4,606,909 A 8/1986 Bechgaard et al.
(Continued)

FOREIGN PATENT DOCUMENTS

CN 102077936 A 6/2011
EP 1685833 A1 8/2006
(Continued)

OTHER PUBLICATIONS

Bannowsky, A. et al., Recovery of erectile function after nerve-sparing radical prostatectomy: improvement with nightly low-dose sildenafil. BJU Int., Feb. 18, 2008, vol. 101, No. 10, pp. 1279-1283.
(Continued)

*Primary Examiner* — Trevor Love
(74) *Attorney, Agent, or Firm* — Wilson Sonsini Goodrich & Rosati

(57) ABSTRACT

The present invention provides for compositions, methods and kits for regulating energy metabolism. In one aspect, the invention provides for compositions that comprise a combination of (a) branched chain amino acids, such as leucine, and (b) vitamin B6, or any precursors or metabolites of (a) or (b). These combinations may be synergistic and/or effective for reducing weight or adipose volume. In another aspect, the invention provides for methods of regulating energy metabolism by the administration of one or more compositions comprising branched chain amino acids and vitamin B6. The invention also provides for kits comprising compositions of branched chain amino acids and vitamin B6 packaged in an oral dose form with usage instructions.

16 Claims, 10 Drawing Sheets

Related U.S. Application Data continuation of application No. 13/662,345, filed on Oct. 26, 2012, now Pat. No. 9,198,454.

(60) Provisional application No. 61/608,595, filed on Mar. 8, 2012, provisional application No. 61/656,407, filed on Jun. 6, 2012.

(51) Int. Cl.

| | | |
|---|---|---|
| *A23L 33/15* | (2016.01) | |
| *A61K 31/194* | (2006.01) | |
| *A61K 31/191* | (2006.01) | |
| *A61K 31/198* | (2006.01) | |
| *A61K 31/155* | (2006.01) | |

(52) U.S. Cl.
CPC .......... *A61K 31/155* (2013.01); *A61K 31/191* (2013.01); *A61K 31/194* (2013.01); *A61K 31/198* (2013.01); *A23V 2002/00* (2013.01)

(56) References Cited

U.S. PATENT DOCUMENTS

| | | | |
|---|---|---|---|
| 4,769,027 A | 9/1988 | Baker et al. | |
| 4,897,268 A | 1/1990 | Tice et al. | |
| 4,992,470 A | 2/1991 | Nissen | |
| 5,087,624 A | 2/1992 | Boynton et al. | |
| 5,250,534 A | 10/1993 | Bell et al. | |
| 5,339,771 A | 8/1994 | Axelrod | |
| 5,395,626 A | 3/1995 | Kotwal et al. | |
| 5,419,283 A | 5/1995 | Leo | |
| 5,616,569 A | 4/1997 | Reinhart | |
| 5,886,012 A | 3/1999 | Pang et al. | |
| 6,004,996 A | 12/1999 | Shah et al. | |
| 6,031,000 A | 2/2000 | Nissen et al. | |
| 6,048,903 A | 4/2000 | Toppo | |
| 6,063,820 A | 5/2000 | Cavazza | |
| 6,224,861 B1 | 5/2001 | Abe et al. | |
| 6,280,779 B1 | 8/2001 | Nadeau et al. | |
| 6,338,862 B1 | 1/2002 | Niazi | |
| 6,369,042 B1 | 4/2002 | Oberthur et al. | |
| 6,384,087 B1 | 5/2002 | Zemel et al. | |
| 6,391,375 B1 | 5/2002 | Fone | |
| 6,469,012 B1 | 10/2002 | Ellis et al. | |
| 6,517,877 B2 | 2/2003 | Gannon | |
| 6,527,711 B1 | 3/2003 | Stivoric et al. | |
| 6,595,929 B2 | 7/2003 | Stivoric et al. | |
| 6,605,038 B1 | 8/2003 | Teller et al. | |
| 6,635,268 B2 | 10/2003 | Peery et al. | |
| 6,638,545 B1 | 10/2003 | Rombi | |
| 6,764,697 B1 | 7/2004 | Jao et al. | |
| 6,790,869 B2 | 9/2004 | Ghai et al. | |
| 6,797,283 B1 | 9/2004 | Edgren et al. | |
| 6,919,373 B1 | 7/2005 | Lam et al. | |
| 6,923,800 B2 | 8/2005 | Chen et al. | |
| 6,929,803 B2 | 8/2005 | Wong et al. | |
| 6,939,556 B2 | 9/2005 | Lautenbach | |
| 7,020,508 B2 | 3/2006 | Stivoric et al. | |
| 7,109,198 B2 | 9/2006 | Gadde et al. | |
| 7,141,254 B2 | 11/2006 | Bhaskaran et al. | |
| 7,153,262 B2 | 12/2006 | Stivoric et al. | |
| 7,230,009 B2 | 6/2007 | Haque et al. | |
| 7,261,690 B2 | 8/2007 | Teller et al. | |
| 7,285,090 B2 | 10/2007 | Stivoric et al. | |
| 7,354,738 B2 | 4/2008 | Spielgelman et al. | |
| 7,495,101 B2 | 2/2009 | Fischesser et al. | |
| 7,502,643 B2 | 3/2009 | Farringdon et al. | |
| 7,674,485 B2 | 3/2010 | Bhaskaran et al. | |
| 7,689,437 B1 | 3/2010 | Teller et al. | |
| 7,744,930 B2 | 6/2010 | Fisher et al. | |
| 7,829,556 B2 | 11/2010 | Bemis et al. | |
| 7,855,289 B2 | 12/2010 | Nunes et al. | |
| 7,893,086 B2 | 2/2011 | Bemis et al. | |
| 7,959,567 B2 | 6/2011 | Stivoric et al. | |
| 7,989,007 B2 | 8/2011 | Giuliano et al. | |
| 8,008,458 B2 | 8/2011 | Zaloga et al. | |
| 8,017,634 B2 | 9/2011 | Sinclair et al. | |
| 8,044,198 B2 | 10/2011 | Nunes et al. | |
| 8,073,707 B2 | 12/2011 | Teller et al. | |
| 8,088,043 B2 | 1/2012 | Andren et al. | |
| 8,088,044 B2 | 1/2012 | Tchao et al. | |
| 8,088,928 B2 | 1/2012 | Nunes et al. | |
| 8,093,401 B2 | 1/2012 | Nunes et al. | |
| 8,106,097 B2 | 1/2012 | Najib | |
| 8,157,731 B2 | 4/2012 | Teller et al. | |
| 8,275,635 B2 | 9/2012 | Stivoric et al. | |
| 8,299,083 B2 | 10/2012 | Kass et al. | |
| 8,369,936 B2 | 2/2013 | Farringdon et al. | |
| 8,370,549 B2 | 2/2013 | Burton et al. | |
| 8,382,590 B2 | 2/2013 | Stivoric et al. | |
| 8,398,546 B2 | 3/2013 | Pacione et al. | |
| 8,403,845 B2 | 3/2013 | Stivoric et al. | |
| 8,408,436 B2 | 4/2013 | Berry et al. | |
| 8,469,862 B2 | 6/2013 | Andren et al. | |
| 8,517,896 B2 | 8/2013 | Robinette et al. | |
| 8,557,869 B2 | 10/2013 | Yamka et al. | |
| 8,562,489 B2 | 10/2013 | Burton et al. | |
| 8,597,677 B2 | 12/2013 | Yamka et al. | |
| 8,617,886 B2 | 12/2013 | Zemel et al. | |
| 8,623,924 B2 | 1/2014 | Zemel et al. | |
| 9,072,692 B2 | 7/2015 | Zemel et al. | |
| 9,198,454 B2 | 12/2015 | Zemel et al. | |
| 9,198,883 B1 | 12/2015 | Zemel et al. | |
| 9,351,967 B2 | 5/2016 | Zemel et al. | |
| 9,408,410 B2 | 8/2016 | Zemel et al. | |
| 2003/0187055 A1 | 10/2003 | Riker et al. | |
| 2004/0120983 A1 | 6/2004 | Connolly | |
| 2004/0186046 A1 | 9/2004 | Burgess et al. | |
| 2005/0064070 A1 | 3/2005 | Liebrecht | |
| 2005/0100617 A1 | 5/2005 | Malnoe et al. | |
| 2005/0112217 A1 | 5/2005 | Khoo | |
| 2005/0215882 A1 | 9/2005 | Chenevert et al. | |
| 2006/0051416 A1 | 3/2006 | Rastogi et al. | |
| 2006/0111435 A1 | 5/2006 | Sinclair et al. | |
| 2006/0159746 A1 | 7/2006 | Troup et al. | |
| 2006/0205633 A1 | 9/2006 | Nishitani et al. | |
| 2007/0014833 A1 | 1/2007 | Milburn et al. | |
| 2007/0065512 A1 | 3/2007 | Dedhiya et al. | |
| 2007/0077310 A1 | 4/2007 | Zemel et al. | |
| 2007/0092577 A1 | 4/2007 | Zemel et al. | |
| 2007/0110850 A1 | 5/2007 | Rifkin | |
| 2007/0203083 A1 | 8/2007 | Mootha et al. | |
| 2007/0244202 A1 | 10/2007 | Murase | |
| 2007/0286909 A1 | 12/2007 | Smith et al. | |
| 2008/0076828 A1 | 3/2008 | Dalton et al. | |
| 2008/0176822 A1 | 7/2008 | Chen | |
| 2008/0220092 A1 | 9/2008 | Dipierro et al. | |
| 2008/0233244 A1 | 9/2008 | Swenson | |
| 2008/0233245 A1 | 9/2008 | White et al. | |
| 2008/0268038 A1 | 10/2008 | Wolfe | |
| 2008/0286254 A1 | 11/2008 | Sakamoto et al. | |
| 2009/0054450 A1 | 2/2009 | Currie et al. | |
| 2009/0105246 A1 | 4/2009 | Bemis et al. | |
| 2009/0142336 A1 | 6/2009 | Walsh et al. | |
| 2009/0156648 A1 | 6/2009 | Molino et al. | |
| 2009/0163476 A1 | 6/2009 | Milburn et al. | |
| 2009/0306222 A1 | 12/2009 | Burton et al. | |
| 2010/0009992 A1 | 1/2010 | Bimberg et al. | |
| 2010/0158956 A1 | 6/2010 | Komorowski | |
| 2010/0173024 A1 | 7/2010 | McDaniel | |
| 2010/0204204 A1 | 8/2010 | Zaworotko et al. | |
| 2010/0210692 A1 | 8/2010 | Farmer et al. | |
| 2010/0316679 A1 | 12/2010 | Sinclair et al. | |
| 2011/0020443 A1 | 1/2011 | Liu et al. | |
| 2011/0027416 A1 | 2/2011 | Sunvold et al. | |
| 2011/0033559 A1 | 2/2011 | Zemel et al. | |
| 2011/0038948 A1 | 2/2011 | Zemel et al. | |
| 2011/0064712 A1 | 3/2011 | Amato | |
| 2011/0064720 A1 | 3/2011 | Amato | |
| 2011/0070258 A1 | 3/2011 | Jimenez Del et al. | |
| 2011/0082189 A1 | 4/2011 | Sinclair et al. | |
| 2011/0111066 A1 | 5/2011 | Ferguson et al. | |
| 2011/0112047 A1 | 5/2011 | Evans et al. | |
| 2011/0130387 A1 | 6/2011 | Nunes et al. | |

(56) References Cited

U.S. PATENT DOCUMENTS

| | | |
|---|---|---|
| 2011/0165125 A1 | 7/2011 | Pan |
| 2011/0208153 A1 | 8/2011 | Alvey |
| 2011/0300197 A1 | 12/2011 | McGenity et al. |
| 2012/0058088 A1 | 3/2012 | Sardi |
| 2012/0177730 A1 | 7/2012 | Baron et al. |
| 2012/0225139 A1 | 9/2012 | Ferguson et al. |
| 2012/0231087 A1 | 9/2012 | Bruheim et al. |
| 2012/0309716 A1 | 12/2012 | Haramizu et al. |
| 2013/0017283 A1 | 1/2013 | Zemel et al. |
| 2013/0017284 A1 | 1/2013 | Zemel et al. |
| 2013/0151196 A1 | 6/2013 | Yuen et al. |
| 2013/0158369 A1 | 6/2013 | Yuen et al. |
| 2013/0237605 A1 | 9/2013 | Zemel et al. |
| 2014/0057017 A1 | 2/2014 | Yamka et al. |
| 2014/0148488 A1 | 5/2014 | Zemel et al. |
| 2016/0067201 A1 | 3/2016 | Zemel et al. |
| 2016/0073659 A1 | 3/2016 | Zemel et al. |
| 2016/0113915 A1 | 4/2016 | Zemel et al. |

FOREIGN PATENT DOCUMENTS

| | | |
|---|---|---|
| EP | 1818055 A1 | 8/2007 |
| EP | 2308493 A1 | 7/2009 |
| FR | 2710243 A1 | 3/1995 |
| JP | 3219838 B2 | 10/2001 |
| JP | 2005097273 A | 4/2005 |
| JP | 2007306851 A | 11/2007 |
| JP | 2008-063321 A | 3/2008 |
| WO | WO-2004056208 A1 | 7/2004 |
| WO | WO 2004/082401 A1 | 9/2004 |
| WO | WO-2005006890 A2 | 1/2005 |
| WO | WO-2007146124 A2 | 12/2007 |
| WO | WO-2007146313 A1 | 12/2007 |
| WO | WO 2011/051974 A1 | 5/2011 |
| WO | WO-2011087708 A1 | 7/2011 |
| WO | WO-2012060884 A1 | 5/2012 |
| WO | WO 2012/097064 A1 | 7/2012 |

OTHER PUBLICATIONS

International Search report and Written opinion dated Sep. 19, 2016 for Singapore Application No. 11201503774P.
Shalwala, M. B., A novel role of sirt1 in sildenafil induced cardio protection in mice. Virginia Commonwealth University—Master Thesis, May 2010, pp. 1-56.
U.S. Appl. No. 14/442,711, filed May 13, 2015, Zemel et al.
U.S. Appl. No. 15/164,647, filed May 25, 2016, Zemel et al.
Agarwal. Cortisol metabolism and visceral obesity: role of 11beta-hydroxysteroid dehydrogenase type I enzyme and reduced co-factor NADPH. Endocr Res. Nov. 2003;29(4):411-8.
Alwine, et al. Method for detection of specific RNAs in agarose gels by transfer to diazobenzyloxymethyl-paper and hybridization with DNA probes. Proc Natl Acad Sci U S A. Dec. 1977;74(12):5350-4.
Amstad, et al. Mechanism of c-fos induction by active oxygen. Cancer Res. Jul. 15, 1992;52(14):3952-60.
Anthony, et al. Orally Administered Leucine Stimulates Protein Synthesis of Skeletal Muscle of Postabsorptive Rats in Association with Increased eIF4F Formation'2. The Journal of Nutrition. 2000; 130:139-145.
Argiles, et al. Cross-talk between skeletal muscle and adipose tissue: a link with obesity? Med Res Rev. Jan. 2005;25(1):49-65.
Atabek, et al. Oxidative stress in childhood obesity. J Pediatr Endocrinol Metab. Aug. 2004; 17(8):1063-8.
Ayala, et al. Chronic treatment with sildenafil improves energy balance and insulin action in high fat-fed conscious mice. Diabetes. Apr. 2007;56(4):1025-33. Epub Jan. 17, 2007.
Banakar, et al. 1alpha, 25-dihydroxyvitamin D3 prevents DNA damage and restores antioxidant enzymes in rat hepatocarcinogenesis induced by diethylnitrosamine and promoted by phenobarbital. World J Gastroenterol. May 1, 2004;10(9):1268-75.

Berchtold. A simple method for direct cloning and sequencing cDNA by the use of a single specific oligonucleotide and oligo(dT) in a polymerase chain reaction (PCR). Nucleic Acids Res. Jan. 11, 1989;17(1):453.
Beta-hydroxy Beta-methylbutyrate (HMB). 2009; 1-2. http://exrx.net/Nutrition/Supplements/HMB.html.
Black grape ingredients. Power of resveratrol. Accessed: Sep. 29, 2010. www.blackgrapehealth.com/Tnt37/ingredients.php.
Blum, et al. SIRT1 modulation as a novel approach to the treatment of diseases of aging. J Med Chem. Jan. 27, 2011;54(2):417-32. Epub Nov. 16, 2010.
Bostrum, et al. A PGC1-α-dependent myokine that drives brown-fat-like development of white fat and thermogenesis. Nature. Jan. 11, 2012;481(7382):463-8. doi: 10.1038/nature10777.
Botanical Online 2010, 1-3. http//:www.botanical-online.com/english/plantschemicalagents.htm.
Boustany. Diabetes and grapefruit. 2010. ThinkScienceNow. 1-4. http://www.thinksciencenow.com/blog-post/diabetes-and-grapefruit/.
Brand, et al. Mitochondrial superoxide and aging: uncoupling-protein activity and superoxide production. Biochem Soc Symp. 2004;(71):203-13.
Breastfeeding.com. Q&A How many ounces of breast milk should I pump? 2010; 1-2. http://www.breastfeeding.com/breastfeeding-questions/breastfeeding-pumping-basics/qa/how-many-ounces-of-breast-milk-should-i-pumpp.aspx.
Brookes. Mitochondrial H(+) leak and ROS generation: an odd couple. Free Radic Biol Med. Jan. 1, 2005;38(1):12-23.
Bruckbauer, et al. Synergistic effects of leucine and resveratrol on insulin sensitivity and fat metabolism in adipocytes and mice. Nutr Metab (Lond). Aug. 22, 2012;9(1):77. doi: 10.1186/1743-7075-9-77.
Bruckbauer, et al. Synergistic effects of metformin, resveratrol, and hydroxymethylbutyrate on insulin sensitivity. Diabetes Metab Syndr Obes. 2013;6:93-102. doi: 10.2147/DMSO.S40840. Epub Feb. 13, 2013.
Bruckbauer, et al. The effects of daily components on energy partitioning and metabolic risk in mice: a microarray study. J Nutrigenet Nutrigenomics. 2009;2(2):64-77. Epub Mar. 4, 2009.
Busquets, et al. Interleukin-15 decreases proteolysis in skeletal muscle: a direct effect. Int J Mol Med. Sep. 2005;16(3):471-6.
Carbo, et al. Interleukin-15 antagonizes muscle protein waste in tumour-bearing rats. Br J Cancer. Aug. 2000;83(4):526-31.
Carbo, et al. Interleukin-15 mediates reciprocal regulation of adipose and muscle mass: a potential role in body weight control. Biochim Biophys Acta. Apr. 3, 2001;1526(1):17-24.
Cerutti, et al. The role of the cellular antioxidant defense in oxidant carcinogenesis. Environ Health Perspect. Dec. 1994;102 Suppl 10:123-9.
Chang, et al. Mammalian MAP kinase signalling cascades. Nature. Mar. 1, 2001;410(6824):37-40.
Cheng, et al. Leucine deprivation decreases fat mass by stimulation of lipolysis in white adipose tissue and upregulation of uncoupling protein 1 (UCP1) in brown adipose tissue. Diabetes. Jan. 2010;59(1):17-25. Epub Oct. 15, 2009.
Chung, et al. Contribution of polyol pathway to diabetes-induced oxidative stress. J Am Soc Nephrol. Aug. 2003;14(8 Suppl 3):S233-6.
Clement, et al. Weight loss regulates inflammation-related genes in white adipose tissue of obese subjects. FASEB J. Nov. 2004;18(14):1657-69.
Cottam, et al. The chronic inflammatory hypothesis for the morbidity associated with morbid obesity: implications and effects of weight loss. Obes Surg. May 2004;14(5):589-600.
De Souza, et al. Insulin secretory defect in zucker FA/FA rats is improved by ameliorating insulin resistance. Diabetes. Aug. 1995;44(8):984-91.
Ding, et al. Amino acid composition of lactating mothers' milk and confinement diet in rural North China. Asia Pac J. Clin Nutr. 2010; 19(3):344-349.

(56) References Cited

OTHER PUBLICATIONS

Doi, et al. Isoleucine, a Blood Glucose-Lowering Amino Acid, Increases Glucose Uptake in Rat Skeletal Muscle in the Absence of Increases in AMP-Activated Protein Kinase Activity. J Nutr. Sep. 2005;135(9):2103-8.
Donato, et al. Effects of leucine supplementation on the body composition and protein status of rats submitted to food restriction. Nutrition. May 2006;22(5):520-7.
Duval, et al. Increased reactive oxygen species production with antisense oligonucleotides directed against uncoupling protein 2 in murine endothelial cells. Biochem Cell Biol. 2002;80(6):757-64.
Emerging risk factors collaboration. Diabetes mellitus, fasting glucose, and risk of cause-specific death. N Engl J Med. Mar. 3, 2011;364(9):829-41.
Erlanson-Albertsson. The role of uncoupling proteins in the regulation of metabolism. Acta. Physiol Scand. Aug. 2003;178(4):405-12.
Ermak, et al. Calcium and oxidative stress: from cell signaling to cell death. Mol Immunol. Feb. 2002;38(10):713-21.
European search report and opinion dated Mar. 9, 2015 for EP Application No. 12814141.3.
Fain, et al. Comparison of the release of adipokines by adipose tissue, adipose tissue matrix, and adipocytes from visceral and subcutaneous abdominal adipose tissues of obese humans. Endocrinology. May 2004;145(5):2273-82. Epub Jan. 15, 2004.
Feige, et al. Specific SIRT1 activation mimics low energy levels and protects against diet-induced metabolic disorders by enhancing fat oxidation. Supplemental information. Cell Metab. Nov. 2008;8(5):347-58.
Feige, et al. Specific SIRT1 activation mimics low energy levels and protects against diet-induced metabolic disorders by enhancing fat oxidation. Cell Metab. Nov. 2008;8(5):347-58. Erratum Cell Metab. Feb. 2009;9(2):210.
Flatt, et al. Direct and indirect actions of nutrients in the regulation of insulin secretion from the pancreatic beta cells. Proc Nutr Soc. Dec. 1991;50(3):559-66.
Fortamet (Metaformin Hydrochloride) Extended-Release Tablets Label. http://www.accessdata.fda.gov/drugsatfda_docs/label/2008/021574s010lbl.pdf. Accessed Jul. 6, 2015.
Fried, et al. Omental and subcutaneous adipose tissues of obese subjects release interleukin-6: depot difference and regulation by glucocorticoid. J Clin Endocrinol Metab. Mar. 1998;83(3):847-50.
Furukawa, et al. Increased oxidative stress in obesity and its impact on metabolic syndrome. J Clin Invest. Dec. 2004;114(12):1752-61.
Gerlinger-Romero, et al. Chronic supplementation of beta-hydroxy-beta methylbutyrate (HMβ) increases the activity of the GH/IGF-I axis and induces hyperinsulinemia in rats. Growth Horm IGF Res. Apr. 2011;21(2):57-62. doi: 10.1016/j.ghir.2010.12.006. Epub Jan. 14, 2011.
Girl, et al. Constitutive activation of NF-kappaB causes resistance to apoptosis in human cutaneous T cell lymphoma HuT-78 cells. Autocrine role of tumor necrosis factor and reactive oxygen intermediates. J Biol Chem. May 29, 1998;273(22):14008-14.
Goldman, et al. Generation of reactive oxygen species in a human keratinocyte cell line: role of calcium. Arch Biochem Biophys. Feb. 1, 1998;350(1):10-8.
Golds function. et al. Adiponectin: A novel adipokine linking adipocytes and vascular Clin Endocrinol Metab. Jun. 2004;89(6):2563-8.
Gordeeva, et al. Cross-talk between reactive oxygen species and calcium in living cells. Biochemistry (Mosc). Oct. 2003;68(10):1077-80.
Hale, et al. Transfer of metforimin into human milk. Diabetologia. 2002; 45:1509-1514.
Harwood, et al. Isozyme-nonselective N-Substituted Bipiperidylcarboxamide Acetyl-CoA Carboxylase Inhibitors Reduce Tissue Malonyl-CoA Concentrations, Inhibit Fatty Acid Synthesis, and Increase Fatty Acid Oxidation in Cultured Cells and in Experimental Animals. The Journal of Biological Chemistry. Sep. 26, 2003; 278(39):37099-37111.
Hollander, et al. Induction of fos RNA by DNA-damaging agents. Cancer Res. Apr. 1, 1989;49(7):1687-92.
Hotamisligil, et al. Tumor necrosis factor alpha inhibits signaling from the insulin receptor. Proc Natl Acad Sci U S A. May 24, 1994;91(11):4854-8.
Howells, et al. Phase I randomized, double-blind pilot study of micronized resveratrol (SRT501) in patients with hepatic metastases—safety, pharmacokinetics, and pharmacodynamics. Cancer Prev Res (Phila). Sep. 2011;4(9):1419-25. Epub Jun. 16, 2011.
Hydroxymethyl Butyrate (HMB). Beth Israel Deaconess Medical Center. Accessed Dec. 13, 2012. http://www.bidmc.org/YourHealth/HolisticHealth/HerbsandSupplements.aspx?ChunkID=21551.
Inoguchi, et al. High glucose level and free fatty acid stimulate reactive oxygen species production through protein kinase C—dependent activation of NAD(P)H oxidase in cultured vascular cells. Diabetes. Nov. 2000;49(11):1939-45.
International search report and written opinion dated May 28, 2013 for PCT Application No. US2013/030044.
International search report and written opinion dated Feb. 8, 2007 for PCT Application No. US2006/038854.
International search report and written opinion dated Mar. 10, 2014 for PCT Application No. US2013/069957.
International search report and written opinion dated Nov. 29, 2012 for PCT Application No. US2012/046814.
Khan, et al. Induction of renal oxidative stress and cell proliferation response by ferric nitrilotriacetate (Fe-NTA): diminution by soy isoflavones. Chem Biol Interact. Aug. 10, 2004;149(1):23-35.
Kiens. Skeletal Muscle Lipid Metabolism in Exercise and Insulin Resistance. Physiological Reviews. 2006;86: 205-243.
Koren, et al. Vitamin D is a prooxidant in breast cancer cells. Cancer Res. Feb. 15, 2001;61(4):1439-44.
Korshunov, et al. High protonic potential actuates a mechanism of production of reactive oxygen species in mitochondria. FEBS Lett. Oct. 13, 1997;416(1):15-8.
Kouzarides, et al. Leucine zippers of fos, jun and GCN4 dictate dimerization specificity and thereby control DNA binding. Nature. Aug. 17, 1989;340(6234):568-71.
Krishnaswamy, et al. Effect of vitamin B6 on leucine-induced changes in human subjects. Am J Clin Nutr. Feb. 1976;29(2):177-81.
Layman. The role of leucine in weight loss diets and glucose homeostasis. Journal of Nutrition, 2003, 133, 261S-267S.
Lee, et al. The evolving role of inflammation in obesity and the metabolic syndrome. Curr Diab Rep. Feb. 2005;5(1):70-5.
Leenders, et al. Leucine as a pharmaconutrient to prevent and treat sarcopenia and type 2 diabetes. Nutr Rev. Nov. 2011;69(11):675-89. doi: 10.1111/j.1753-4887.2011.00443.x. Abstract only.
Li, et al. Evaluation of antioxidant capacity and aroma quality of breast milk. Nutrition. 2008; 25(1):1-3.
Li, et al. Leucine nutrition in animals and humans: mTOR signaling and beyond. Amino Acids. Nov. 2011;41(5):1185-93. Epub Jul. 20, 2011.
Li, et al. Visceral fat: higher responsiveness of fat mass and gene expression to calorie restriction than subcutaneous fat. Exp Biol Med (Maywood). Nov. 2003;228(10):1118-23.
Lin, et al. Increased oxidative damage with altered antioxidative status in type 2 diabetic patients harboring the 16189 T to C variant of mitochondrial DNA. Ann N Y Acad Sci. May 2005;1042:64-9.
Lin. Suppression of protein kinase C and nuclear oncogene expression as possible action mechanisms of cancer chemoprevention by Curcumin. Arch Pharm Res. Jul. 2004;27(7):683-92.
Lind, et al. Evaluation of four different methods to measure endothelium-dependent vasodilation in the human peripheral circulation. Clin Sci (Lond). May 2002;102(5):561-7.
Lira, et al. Nitric oxide and AMPK cooperatively regulate PGC-1 in skeletal muscle cells. J Physiol. Sep. 15, 2010;588(Pt 18):3551-66. Epub Jul. 19, 2010.
Lumeng, et al. Plasma content of B6 vitamers and its relationship to hepatic vitamin B6 metabolism. J Clin Invest. Oct. 1980; 66(4): 688-695.
Lynch, et al. Leucine is a direct-acting nutrient signal that regulates protein synthesis in adipose tissue. Am J Physiol Endocrinol Metab. Sep. 2002;283(3):E503-13.

(56) References Cited

OTHER PUBLICATIONS

Macotela, et al. Dietary Leucine—an environmental modifier of insulin resistance acting on multiple levels of metabolism. PLoS One. 2011;6(6):e21187. Epub Jun. 22, 2011.

Mahadev, et al. The NAD(P)H oxidase homolog Nox4 modulates insulin-stimulated generation of H2O2 and plays an integral role in insulin signal transduction. Mol Cell Biol. Mar. 2004;24(5):1844-54.

Manders, et al. Nutrition and disease co-ingestion of a protein hydrolysate with or without additional leucine effectively reduces postprandial blood glucose excursions in type 2 diabetic men 1. Jan. 1, 2006. 1294-1299. http://jn.nutrition.org/content/136/5/1294.full.pdf.

Manea, et al. Changes in oxidative balance in rat pericytes exposed to diabetic conditions. J Cell Mol Med. Jan.-Mar. 2004;8(1):117-26.

Melnik. Leucine signaling in the pathogenesis of type 2 diabetes and obesity. World J Diabetes. Mar. 15, 2012;3(3):38-53. doi: 10.4239/wjd.v3.i3.38.

Melton, et al. Efficient in vitro synthesis of biologically active RNA and RNA hybridization probes from plasmids containing a bacteriophage SP6 promoter. Nucleic Acids Res. Sep. 25, 1984;12(18):7035-56.

Merck Manual Home Edition online article entitled, "Multiple Sclerosis"—accessed Jun. 20, 2010 at http://www.merck.com/mmhe/print/sec06/ch092/ch092b.html.

Merck Manual Home Edition online article entitled, "Introduction: Coronary Artery Disease"—accessed Jun. 20, 2010 at www.merck.com/mmhe/print/sec03/ch033/ch033a.html.

Miwa, et al. Mitochondrial matrix reactive oxygen species production is very sensitive to mild uncoupling. Biochem Soc Trans. Dec. 2003;31(Pt 6):1300-1.

Morris, et al. 1,25-dihydroxyvitamin D3 modulation of adipocyte glucocorticoid function. Obes Res. Apr. 2005;13(4):670-7.

Nairizi, et al. Leucine supplementation of drinking water does not alter susceptibility to diet-induced obesity in mice. Nutr. Apr. 2009;139(4):715-9. Epub Feb. 25, 2009.

Nisoli, et al. Mitochondrial biogenesis by NO yields functionally active mitochondria in mammals Proc Natl Acad Sci U S A. Nov. 23, 2004;101(47):16507-12. Epub Nov. 15, 2004.

Nisoli, et al. Mitochondrial biogenesis in mammals: the role of endogenous nitric oxide. Science. Feb. 7, 2003;299(5608):896-9.

Nomura, et al. Inhibition of 12-O-tetradecanoylphorbol-13-acetate-induced NF-kappaB activation by tea polyphenols, (-)-epigallocatechin gallate and theaflavins. Carcinogenesis. Oct. 2000;21(10):1885-90.

Notice of allowance dated Mar. 6, 2015 for U.S. Appl. No. 13/866,936.

Notice of allowance dated Mar. 15, 2013 for U.S. Appl. No. 13/549,381.

Notice of allowance dated Apr. 29, 2015 for U.S. Appl. No. 13/866,936.

Notice of allowance dated May 29, 2013 for U.S. Appl. No. 13/549,399.

Notice of allowance dated Aug. 13, 2013 for U.S. Appl. No. 13/549,381.

Notice of allowance dated Aug. 15, 2013 for U.S. Appl. No. 13/549,399.

Notice of allowance dated Dec. 28, 2012 for U.S. Appl. No. 13/549,399.

Ofei, et al. Effects of an engineered human anti-TNF-alpha antibody (CDP571) on insulin sensitivity and glycemic control in patients with NIDDM. Diabetes. Jul. 1996;45(7):881-5.

Office action dated Jun. 25, 2010 for U.S. Appl. No. 11/543,171.

Office action dated Nov. 7, 2012 for U.S. Appl. No. 13/549,381.

Office action dated Dec. 23, 2010 for U.S. Appl. No. 11/543,171.

Panichi, et al. Calcitriol modulates in vivo and in vitro cytokine production: a role for intracellular calcium. Kidney Int. Nov. 1998;54(5):1463-9.

Park, et al. Resveratrol ameliorates aging-related metabolic phenotypes by inhibiting cAMP phosphodiesterases. Cell. Feb. 3, 2012;148(3):421-33.

Pearce, et al. Sports supplements: A modern case of caveat emptor. Current Sports Medicine Reports. 2005; 4:171-178.

Peterson, et al. The mechanism of transamination. Function of the histidyl residue at the active site of supernatant aspartate transaminase. J Biol Chem. Feb. 25, 1970;245(4):806-13.

Povolny, et al. The role of recombinant human M-CSF, IL-3, GM-CSF and calcitriol in clonal development of osteoclast precursors in primate bone marrow. Exp Hematol. Apr. 1993;21(4):532-7.

Price, et al. SIRT1 is required for AMPK activation and the beneficial effects of resveratrol on mitochondrial function. Cell Metab. May 2, 2012;15(5):675-90. doi: 10.1016/j.cmet.2012.04.003.

Quinn, et al. Interleukin-15 stimulates adiponectin secretion by 3T3-L1 adipocytes: evidence for a skeletal muscle-to-fat signaling pathway. Cell Biol Int. Jun. 2005;29(6):449-57.

Rasmussen, et al. Regulation of fatty acid oxidation in skeletal muscle. Annu Rev Nutr. 1999;19:463-84.

Reeves. Components of the AIN-93 diets as improvements in the AIN-76A diet. J Nutr. May 1997;127(5 Suppl):838S-841S.

Remington's Pharmaceutical Sciences, 18th Edition, 1990, Mack Publishing Co.

Roberts, et al. Nutrition and aging: changes in the regulation of energy metabolism with aging Physiol Rev. Apr. 2006;86(2):651-67.

Sabatini, et al. Tadalafil alters energy metabolism in C2C12 skeletal muscle cells. Acta Biochim Pol. 2011;58(2):237-41. Epub Jun. 16, 2011.

Schulze-Osthoff, et al. Oxidative stress and signal transduction. Int J Vitam Nutr Res. 1997;67(5):336-42.

Sellden, et al. Augmented thermic effect of amino acids under general anaesthesia: a mechanism useful for prevention of anaesthesia-induced hypothermia. Clin Sci (Lond). May 1994;86(5):611-8.

Shangari, et al. The cytotoxic mechanism of glyoxal involves oxidative stress. Biochem Pharmacol. Oct. 1, 2004;68(7): 1433-42.

Shi, et al. 1alpha,25-dihydroxyvitamin D3 inhibits uncoupling protein 2 expression in human adipocytes. FASEB J. Nov. 2002;16(13):1808-10. Epub Sep. 5, 2002.

Shi, et al. 1alpha,25-Dihydroxyvitamin D3 modulates human adipocyte metabolism via nongenomic action. FASEB J. Dec. 2001;15(14):2751-3. Epub Oct. 15, 2001.

Simeone, et al. How retinoids regulate breast cancer cell proliferation and apoptosis. Cell Mol Life Sci. Jun. 2004;61(12):1475-84.

Soares, et al. Effects of oxidative stress on adiponectin secretion and lactate production in 3T3-L1 adipocytes. Free Radic Biol Med. Apr. 1, 2005;38(7):882-9.

Solerte, et al. Metabolic effects of orally administered amino acid mixture in elderly subjects with poorly controlled type 2 diabetes mellitus. Am J Cardiol. Apr. 22, 2004;93(8A):23A-29A.

Song, et al. Methionine-induced hyperhomocysteinemia promotes superoxide anion generation and NFkappaB activation in peritoneal macrophages of C57BL/6 mice. J Med Food. 2004 Summer;7(2):229-34.

Sonta, et al. Evidence for contribution of vascular NAD(P)H oxidase to increased oxidative stress in animal models of diabetes and obesity. Free Radic Biol Med. Jul. 1, 2004;37(1):115-23.

Sorescu, et al. Superoxide production and expression of nox family proteins in human atherosclerosis. Circulation. Mar. 26, 2002;105(12):1429-35.

Stipanuk. Leucine and protein synthesis: mTOR and beyond. Nutr Rev. Mar. 2007;65(3):122-9.

Sun, et al. 1, 25(OH)2D3 and reactive oxygen species interatively stimulate angiotensinogen expression in differentiated 3T3-L1 adipocytes. FASEB J. 2005; 19:A70, No. 67.8 (abstract only).

Sun, et al. Calcium and dairy products inhibit weight and fat regain during ad libitum consumption following energy restriction in Ap2-agouti transgenic mice. J Nutr. Nov. 2004;134(11):3054-60.

Sun, et al. Dietary calcium regulates ROS production in aP2-agouti transgenic mice on high-fat/high-sucrose diets. Int J Obes (Lond). Sep. 2006;30(9):1341-6. Epub Mar. 7, 2006.

(56) References Cited

OTHER PUBLICATIONS

Sun, et al. Dual effects of 1-alpha,25-(OH)2-D3 on adipocyte apoptosis. FASEB J. 2004; 18:A49 (abstract only).
Sun, et al. Effects of mitochondrial uncoupling on adipocyte intracellular Ca(2+) and lipid metabolism. J Nutr Biochem. Apr. 2003;14(4):219-26.
Sun, et al. Leucine and calcium regulate fat metabolism and energy partitioning in murine adipocytes and muscle cells. Lipids. Apr. 2007;42(4):297-305. Epub Feb. 20, 2007.
Sun, et al. Leucine modulation of mitochondrial mass and oxygen consumption in skeletal muscle cells and adipocytes. Nutr Metab (Lond). Jun. 5, 2009;6:26. doi:10.1186/1743-7075-6-26.
Sun, et al. Reactive oxygen species stimulate cell proliferation and down-regulate UCP2 expression in 3T3-L1 adipocytes. Obesity Research. 2004; 11: A21, No. 80-OR (abstract only).
Sun, et al. Role of uncoupling protein 2 (UCP2) expression and lalpha, 25-dihydroxyvitamin D3 in modulating adipocyte apoptosis. FASEB J. Sep. 2004;18(12):1430-2. Epub Jul. 1, 2004.
Suzuki, et al. Oxidants as stimulators of signal transduction. Free Radic Biol Med. 1997;22(1-2):269-85.
Suzuki, et al. Relationship between obesity and serum markers of oxidative stress and inflammation in Japanese. Asian Pac J Cancer Prey. Jul.-Sep. 2003;4(3):259-66.
Tappy, et al. Thermic effect of infused amino acids in healthy humans and in subjects with insulin resistance. Am J Clin Nutr. Jun. 1993;57(6):912-6.
Tennen, et al. Finding a target for resveratrol. Cell. Feb. 3, 2012;148(3):387-9.
Thannickal, et al. Reactive oxygen species in cell signaling. Am J Physiol Lung Cell Mol Physiol. Dec. 2000;279(6):L1005-28.
Thompson, et al. Effect of energy-reduced diets high in dairy products and fiber on weight loss in obese adults. Obes Res. Aug. 2005;13(8):1344-53.
Thomson, et al. Effects of nine weeks of beta-hydroxy-beta-methylbutyrate supplementation on strength and body composition in resistance trained men. Journal of strength and conditioning research / National Strength & Conditioning Association 23: 827-835, 2009.
Upham, et al. Hydrogen peroxide inhibits gap junctional intercellular communication in glutathione sufficient but not glutathione deficient cells. Carcinogenesis. Jan. 1997;18(1):37-42.
Valle, et al. Low-grade systemic inflammation, hypoadiponectinemia and a high concentration of leptin are present in very young obese children, and correlate with metabolic syndrome. Diabetes Metab. Feb. 2005;31(1):55-62.
Van Loon. Leucine as a pharmaconutrient in health and disease. Curr Opin Clin Nutr Metab Care. Jan. 2012;15(1):71-7. Abstract only.
Verdin, et al. Sirtuin regulation of mitochondria: energy production, apoptosis, and signaling. Trends Biochem Sci. Dec. 2010;35(12):669-75. Epub Sep. 20, 2010.
Volk, et al. Transient Ca2+ changes in endothelial cells induced by low doses of reactive oxygen species: role of hydrogen peroxide. Mol Cell Biochem. Jun. 1997;171(1-2):11-21.
Wajchenberg. Subcutaneous and visceral adipose tissue: their relation to the metabolic syndrome. Endocr Rev. Dec. 2000;21(6):697-738.
Weisberg, et al. Obesity is associated with macrophage accumulation in adipose tissue. J Clin Invest. Dec. 2003;112(12):1796-808.
Weitzman, et al. Free radical adducts induce alterations in DNA cytosine methylation. Proc Natl Acad Sci U S A. Feb. 15, 1994;91(4):1261-4.
Wilson, et al. Effects of beta-hydroxy-beta-methylbutyrate (HMB) on exercise performance and body composition across varying levels of age, sex, and training experience: a review. Nutr Metab (Lond). Jan. 3, 2008;5:1.
Wiseman, et al. Damage to DNA by reactive oxygen and nitrogen species: role in inflammatory disease and progression to cancer. Biochem J. Jan. 1, 1996;313 ( Pt 1):17-29.

Xiao, et al. Leucine deprivation increases hepatic insulin sensitivity via GCN2/mTOR/S6K1 and AMPK pathways. Diabetes. Mar. 2011;60(3):746-56. Epub Jan. 31, 2011.
Xu, et al. Chronic inflammation in fat plays a crucial role in the development of obesity-related insulin resistance. J Clin Invest. Dec. 2003;112(12):1821-30.
Xue, et al. Relationship between human adipose tissue agouti and fatty acid synthase (FAS). J Nutr. Oct. 2000;130(10):2478-81.
Xue, et al. The agouti gene product inhibits lipolysis in human adipocytes via a Ca2+-dependent mechanism. FASEB J. Oct. 1998;12(13):1391-6.
Yang, et al. Leucine metabolism in regulation of insulin secretion from pancreatic beta cells. Nutr Rev. May 2010;68(5):270-9.
Zanchi, et al. Potential antiproteolytic effects of L-leucine: observations of in vitro and in vivo studies. Nutr Metab (Lond). Jul. 17, 2008;5:20.
Zemel, et al. Calcium and dairy acceleration of weight and fat loss during energy restriction in obese adults. Obes Res. Apr. 2004;12(4):582-90.
Zemel, et al. Dairy augmentation of total and central fat loss in obese subjects. Int J Obes (Lond). Apr. 2005;29(4):391-7.
Zemel, et al. Effects of dairy compared with soy on oxidative and inflammatory stress in overweight and obese subjects. Am J Clin Nutr. Jan. 2010;91(1):16-22. Epub Nov. 4, 2009.
Zemel, et al. Regulation of adiposity by dietary calcium. FASEB J. Jun. 2000; 14(9):1132-8.
Zemel,et al. Effects of calcium and dairy on body composition and weight loss in African-American adults. Obes Res. Jul. 2005;13(7):1218-25.
Zemel. Calcium and dairy modulation of obesity risk. Obes Res. Jan. 2005;13(1):192-3.
Zemel. Role of calcium and dairy products in energy partitioning and weight management. Am J Clin Nutr. May 2004;79(5):907S-912S.
Zemel. The role of dairy foods in weight management. J Am Coll Nutr. Dec. 2005;24(6 Suppl):537S-46S.
Zhang, et al. Increasing dietary leucine intake reduces diet-induced obesity and improves glucose and cholesterol metabolism in mice via multimechanisms. Diabetes. Jun. 2007;56(6):1647-54. Epub Mar. 14, 2007.
Zhang, et al. Occurrence of beta-hydroxyl-beta-methyl butyrates in foods and feed. Protein and amini acid nutrition. 1994; A464: 2685-2690.
Bender, et al. Cyclic nucleotide phosphodiesterases: molecular regulation to clinical use. Pharmacol Rev. Sep. 2006;58(3):488-520.
BodyBuilding, VitaMinder Power shaker, 2006, BodyBuilding. com, p. 1.
Bruckbauer, et al. Synergistic effects of polyphenols and methylxanthines with leucine on AMPK/sirtuin-mediated metabolism in muscle cells and adipocytes. PLoS One. 9(2):e89166. Feb. 14, 2014.
Chalasani, et al. The diagnosis and management of non-alcoholic fatty liver disease: Practice guideline by the American Association for the Study of Liver Diseases, American College of Gastroenterology, and the American Gastroenterological Association. Hepatology 2012; 55:2005-2021.
European search report and opinion dated May 6, 2016 for EP Application No. 13854549.
European search report and opinion dated Sep. 28, 2015 for EP Application No. 13758140.1.
Festi, et al. Hepatic steastosis in obese patients: clinical aspects and prognostic significance. Obesity Rev 2004; 5:27-42.
Hou, et al. Sirt1 regulates hepatocyte lipid metabolism through activating AMPK-activated protein kinase. J Biol Chem 2008; 383:20015-20026.
International search report and written opinion dated May 22, 2015 for PCT/US2015/018182.
JillWillRun. Hydration Review Nuun, 2009, pp. 1-8.
Notice of allowance dated Feb. 1, 2016 for U.S. Appl. No. 14/927,255.
Notice of allowance dated Apr. 28, 2016 for U.S. Appl. No. 14/927,228.

(56) References Cited

OTHER PUBLICATIONS

Notice of allowance dated Sep. 1, 2015 for U.S. Appl. No. 13/662,345.
Notice of allowance dated Sep. 11, 2015 for U.S. Appl. No. 14/746,516.
Office action dated Feb. 5, 2015 for U.S. Appl. No. 13/662,345.
Office action dated Apr. 22, 2013 for U.S. Appl. No. 13/662,345.
Office action dated Sep. 16, 2013 for U.S. Appl. No. 13/662,345.
Patterson, et al. Excretion of tryptophan-niacin metabolites by young men: effects of tryptophan, leucine, and vitamin B6 intakes. Am J Clin Nutr. Oct. 1980;33(10):2157-67.
Purushotham, et al. Hepatocyte-specific deletion of Sirt1 alters fatty acid metabolism and results in hepatic steatosis and inflammation. Cell Metabolism 2009; 9:327-338.
S Bear. Nother way to get leucine for the 6 week cure, 2009, pp. 1-5.
Varma, et al. Chronic Tadalafil Therapy Improves Fasting Glucose Levels and Downregulates Microrna-103 and -107 in Obese Diabetic Mice. Circulation. 2012; 126: A14802. Abstract 14802.
Vernon et al. Systematic review: The epidemiology and natural history of non-alcoholic fatty liver disease and non-alcoholic steatohepatitis in adults. Aliment Pharmacol 2011; 34:274-285.
Warner. Metformin Linked to B12 Deficiency, 2009, WebMD, pp. 1-2.
Zoraghi, et al. Phosphodiesterase-5 Gln817 is critical for cGMP, vardenafil, or sildenafil affinity: its orientation impacts cGMP but not cAMP affinity. J Biol Chem. Mar. 3, 2006;281(9):5553-8. Epub Jan. 5, 2006.
"Arend, et al. Inhibition of the production and effects of interleukin-1 and tumor necrosis factor alpha in rheumatoid arthritis. Arthritis Rheum. Feb. 1995;38(2):151-60.".
"Bartges, et al. Calculating a patient's nutritional requirements. Veterinary Medicine. 2004; 99:632.".
"Brennan, et al. Inhibitory effect of TNF alpha antibodies on synovial cell interleukin-1 production in rheumatoid arthritis. Lancet. Jul. 29, 1989;2(8657):244-7.".
"Carroll, et al. Antagonism of the IL-6 cytokine subfamily—a potential strategy for more effective therapy in rheumatoid arthritis. Inflamm Res. Jan. 1998;47(1):1-7.".
European Search Report dated Sep. 21, 2016 for EP Application No. 14767946.8.
"Haworth, et al. Expression of granulocyte-macrophage colony-stimulating factor in rheumatoid arthritis: regulation by tumor necrosis factor-alpha. Eur J Immunol. Oct. 1991;21(10):2575-9.".
"Hornstra, et al. Essential fatty acids in pregnancy and early human development. Eur J Obstet Gynecol Reprod Biol. Jul. 1995;61(1):57-62.".

"International search report with written opinion dated Aug. 22, 2014 for PCT Application No. US2014/018418.".
"Ionut, et al. Novel canine models of obese prediabetes and mild type 2 diabetes. Am J Physiol Endocrinol Metab. Jan. 2010;298(1):E38-48. doi: 10.1152/ajpendo.00466.2009. Epub Oct. 20, 2009.".
"Laflamme. Development and validation of a body condition scor system for dogs. Canine Practice. 1997; 22:10-15.".
"Lim, et al. Intakes of dietary docosahexaenoic acid ethyl ester and egg phosphatidylcholine improve maze-learning ability in young and old mice. J Nutr. Jun. 2000;130(6):1629-32.".
"Mawby, et al. Comparison of various methods for estimating body fat in dogs. J Am Anim Hosp Assoc. Mar.-Apr. 2004;40(2):109-14.".
"Moser, et al. interleukin 1 and tumor necrosis factor stimulate human vascular endothelial cells to promote transendothelial neutrophil passage. J Clin Invest. Feb. 1989;83(2):444-55.".
"Peterson, et al. The mechanism of transamination. Function of the histidyl residue at the active site of supernatant aspartate transaminase. J Biol Chem. Feb. 25, 1970;245(4):806-13.".
Poveromo, J. "Weight-loss ressolve—Natural practitioner magazine", Natural Practitioner, Jan. 1, 2013, pp. 1-4, XP055302353. Retrieved from the internet: URL:http://naturalpractitionermag.com/weight-loss-resolve.Retrieved on Sep. 14, 2016.
"Rogers. A healthy body, a healthy mind: long-term impact of diet on mood and cognitive function. Proc Nutr Soc. Feb. 2001;60(1):135-43.".
"Sunvold, et al. Dietary fiber for dogs: IV. In vitro fermentation of selected fiber sources by dog fecal inoculum and in vivo digestion and metabolism of fiber-supplemented diets. J Anim Sci. Apr. 1995;73(4):1099-109.".
"Yamka, et al. In vivo measurement of flatulence and nutrient digestibility in dogs fed poultry by-product meal, conventional soybean meal, and low-oligosaccharide low-phytate soybean meal. Am J Vet Res. Jan. 2006;67(1):88-94.".
Yamka, R.M. et al., Effects of 3 canine weight loss foods on body composition and obesity markers. Intern J Appl. Res Vet Med, Jan. 1, 2007.; pp. 125-132, XP055302329, Retrieved from the Internet: URL:http://www.jarv,.com/articles/Vol5Iss3/Yamka 125-132.pdf. Retrieved on Sep. 14, 2016.
Yamka, R.M. et al., Identification of canine markers related to obesity and the effects of weight loss on the markers of interest. Intern J Appl Res Vet Med, Jan. 1, 2006, XP055302356, Retrieved form the internet: URL:http://www.jarvm.com/articles/Vol4Iss4/Yamka.pdf. Retrieved on Sep. 14, 2016.
"Yudkin, et al. Inflammation, obesity, stress and coronary heart disease: is interleukin-6 the link? Atherosclerosis. Feb. 2000;148(2):209-14.".

COMPOSITIONS, METHODS, AND KITS FOR REGULATING ENERGY METABOLISM

CROSS-REFERENCE

This application is a continuation application of U.S. application Ser. No. 14/927,228, filed Oct. 29, 2015, which is a continuation application of U.S. application Ser. No. 13/662,345, filed Oct. 26, 2012, now U.S. Pat. No. 9,198,454, which claims benefit of priority to U.S. Provisional Application No. 61/608,595, filed Mar. 8, 2012, and U.S. Provisional Application No. 61/656,407, filed Jun. 6, 2012, all of which are incorporated herein by reference in their entirety for all purposes.

BACKGROUND OF THE INVENTION

Energy metabolism is the transformation of energy that accompanies biochemical reactions in the body. Energy metabolism is often reduced or impaired in animals, particularly aging animals, postmenopausal animals, or animals experiencing health or other problems that cause a reduction in energy metabolism. See, Roberts et. al., Nutrition and Aging: Changes in the Regulation of Energy Metabolism With Aging, Physiol. Rev. 86: 651-667, 2006. In such animals, energy expenditure associated with physical activity and basal metabolic rate generally decreases. Such reduced or impaired energy metabolism often results in increased fat deposition and reduced muscle mass. This occurs even though food and energy intake remain the same. This result increases the risk of many chronic diseases such as type II diabetes, hyperlipidemia, arteriosclerosis, and hypertension; lowers the animal's quality of life; and reduces the animal's life-span.

A number of compositions have been proposed to address the regulation of energy metabolism, including isoflavones (U.S. Patent Application No. 20110165125), pharmaceutical drugs like tetrahydrolipstatin (U.S. Pat. No. 6,004,996), and compositions that modulate the SIRT1 and AMPK pathways (U.S. Patent Application Nos. 20100210692, 20100009992, 20070244202 and 20080176822). Also, shotgun compositions that include a variety of known agents that facilitate regulation of energy have been described (U.S. Patent Application No. 20080220092). Despite this, there still remains a need for effective compositions and methods for safe regulation of energy metabolism.

SUMMARY OF THE INVENTION

The present invention generally relates to the field of regulation of energy metabolism. In some embodiments, the present invention provides for compositions, methods, and kits for regulating energy metabolism using branched chain amino acids and vitamin B6.

The present invention addresses the need for improved compositions and supplements for regulating energy metabolism. The regulation of energy metabolism can allow for decreases in weight or adipose tissue, increases in fat oxidation or insulin sensitivity, and/or the decrease of inflammation or oxidative stress. These effects can be by way of an increase in or regulation of energy metabolism, including cellular metabolism and mitochondrial biogenesis.

In one aspect, the invention provides for a composition comprising (a) one or more types of branched chain amino acids and/or metabolites thereof, and (b) vitamin B6, wherein mass ratio of component (a) to (b) in said composition is greater than about 50, 65, 70, 75, 85, 90, 100, 200 or greater and wherein the composition when administered to a subject in need thereof enhances energy metabolism, including cellular metabolism and mitochondrial biogenesis, as measured by a decrease in weight gain of a subject, a decrease in adipose volume of a subject, an increase in fat oxidation of a subject, an increase in insulin sensitivity of a subject, a decrease in oxidative stress markers of a subject, and/or a decrease in inflammatory markers of a subject. In some embodiments, the mass ratio of component (a) to component (b) in said composition is greater than about 65. In some embodiments, the mass ratio of component (a) to component (b) in said composition is greater than about 65, and component (a) is leucine.

In some embodiments, the composition can be substantially free of non-branched chain amino acids. In some embodiments, the composition is a food composition. In other embodiments, the composition is a dietary supplement packaged as a beverage, solid food or semi-solid food. The composition can be formulated as an oral dosage form. The composition can also further comprise a food carrier. The composition can be a dietary supplement. The composition can be packaged as a unit dosage. The unit dosage can comprise about 1,125 mg of leucine and about 15 mg of vitamin B6. Alternatively, the unit dosage can comprise about 750 mg of leucine and about 10 mg of vitamin B6. In some embodiments, the dosing of leucine can be about 500, 600, 700, 800, 900, 1000, 1100, 1200, 1300, 1400, 1500, 1700, 1900, 2100, or 2300 mg. The dosing of vitamin B6 can be about 0.1, 0.5, 1, 2, 4, 6, 8, 10, 12, 15, 18, 21, 24, 27, 30, or 33 mg. The unit dosage can be formulated as a tablet, extended-release tablet, capsule, or gel capsule. The composition can also comprise a pharmaceutically active agent or other therapeutically active agents. The composition can also comprise an anti-diabetic agent.

In some embodiments, the branched chain amino acid that can be included in the subject compositions is selected from the group consisting of leucine, valine, isoleucine, and 4-hydroxyisoleucine. In other embodiments, the branched chain amino acid is leucine.

Another aspect of the invention provides for a composition comprising: a synergistically effective amount of (a) one or more types of branched chain amino acids and/or metabolites thereof, and (b) vitamin B6, wherein the combination when administered to a subject in need thereof synergistically enhances energy metabolism, including cellular metabolism, and mitochondrial biogenesis, to a greater degree as compared to administering to a subject component (a) or component (b) alone. The composition, when administered to a subject in need thereof, can synergistically enhance energy metabolism, including cellular metabolism and mitochondrial biogenesis, as measured by a decrease in weight gain of a subject, a decrease in adipose volume of a subject, an increase in fat oxidation of a subject, an increase in insulin sensitivity of a subject, a decrease in oxidative stress markers of a subject, and/or a decrease in inflammatory markers of a subject. In some embodiments, the composition is substantially free of non-branched chain amino acids.

The enhanced energy metabolism can be quantified by an increase in fatty acid oxidation of a myotube by at least about 140%, an increase in fatty acid oxidation of an adipocyte by at least about 450%, an increase in glucose utilization of an adipocyte by at least 150%, an increase in glucose utilization of an adipocyte by at least 200%, an increase in Sirt1 expression in a myotube by at least about two-fold, an increase in AMPK activation in a myotube by at least about two-fold, and/or an increase in mitochondrial biomass in a myotube by at least about 50%, when (i) media from the myotube or adipocyte treated with the composition is administered to the other of the myotube or adipocyte or (ii) the composition is administered to the myotube or adipocyte. Additionally, the enhanced energy metabolism can be measured by an increase in weight loss of a subject by at least 40%, an increase in fat loss of a subject by at least about 50%, an increase in fat loss of a subject by at least about 50%, or an increase in insulin sensitivity by at least about 15%, an increase in fat oxidation by at least about 60%, or a decrease in oxidative stress markers by at least about 15%, when the composition is administered to the subject.

In some embodiments, the combination enhances energy metabolism to a greater degree as compared to the sum of the effects of administering component (a) alone and component (b) alone, as if each component (a) and (b) exerted its effect independently. The composition can enhance fatty acid oxidation of a myotube by at least about 50% greater than the predicted additive effect of administering each component alone if each component exerted its effect independently. The composition can enhance glucose utilization of a myotube by at least about 150% greater than the predicted additive effect of administering each component alone if each component exerted its effect independently.

Another aspect of the invention provides for a composition comprising: (a) an amount of one or more types of branched chain amino acids and/or metabolites thereof; and (b) an amount of vitamin B6, wherein the amount of the one or more types of branched chain amino acids and/or metabolites thereof and the amount of vitamin B6 are amounts effective for an enhancement of energy metabolism, including cellular metabolism and mitochondrial biogenesis, as measured by a decrease in weight gain of a subject, a decrease in adipose volume of a subject, an increase in fat oxidation of a subject, an increase in insulin sensitivity of a subject, a decrease in oxidative stress markers of a subject, and/or a decrease in inflammatory markers of a subject. In some embodiments, the amount of the one or more types of branched chain amino acids and/or metabolites thereof is effective to decrease energy storage in adipocytes and/or increase fatty acid oxidation in a subject when administered to the subject. The amount of vitamin B6 can be effective to decrease the activity of fatty acid synthase and/or reduce intracellular calcium concentration within a subject when administered to the subject. In other embodiments, the composition can further comprise a food carrier.

The invention provides for a composition comprising a unit dosage formulated for oral ingestion, the unit dosage comprising: (a) leucine and/or a metabolite thereof; and (b) vitamin B6, wherein the unit dosage is effective for enhancing energy metabolism relative to a baseline level in a subject administered another unit dosage lacking component (a) and component (b) as measured, when said unit dosage is administered to said subject, by an increase in weight loss by at least 40%, an increase in fat loss by at least about 50%, an increase in insulin sensitivity by at least about 10%, an increase in fat oxidation by at least about 60%, or a decrease in oxidative stress markers by at least about 15%. In some embodiments, component (a) is present in an amount of at least about 500 mg, and component (b) is present in an amount of at least about 5 mg. In other embodiments, component (a) is present in an amount of at least about 1130 mg, and component (b) is present in an amount of at least about 12 mg.

In some embodiments, the composition can be packaged as a unit dosage. The composition, which may be packaged as a unit dosage, can comprise (a) at least about 500 mg of one or more types of branched chain amino acids and/or metabolites thereof, and (b) at least about 5 mg of vitamin B6. The branched chain amino acids and/or metabolites thereof can comprise leucine. The unit dosage can comprise about 1,125 mg of leucine and about 15 mg of vitamin B6. In some embodiments, the composition has a shelf-life greater than 7 months. In some embodiments, the composition is in a container and is nonperishable at room temperature for at least one hour after opening. In some embodiments, component (a) is present in an amount of at least 550 mg or at least 1130 mg. In some embodiments, component (b) is present in an amount of at least 7.5 mg or 12 mg. In some embodiments, component (a) is present in an amount of at least about 550 mg, and component (b) is present in an amount of at least about 7.5 mg. In some embodiments, component (a) is present in an amount of at least about 1130 mg, and component (b) is present in an amount of at least about 12 mg. In some embodiments, the composition is a dietary supplement packaged as a beverage, solid food, or semi-solid food. In some embodiments, the composition is formulated as a tablet, capsule, or gel capsule. In some embodiments, the composition comprises one or more of a sweetener, a bulking agent, a stabilizer, an acidulant, and a preservative.

In another aspect, the compositions described here, such as compositions including leucine and B6, can further comprise a pharmaceutically active agent or an anti-diabetic agent. The pharmaceutically active agent or anti-diabetic agent can be metformin. The compositions described, such as a pharmaceutical composition, can further comprise a pharmaceutically acceptable excipient.

In one aspect, the invention provides a kit comprising a combination composition as described herein. In some embodiments, the invention provides for a kit comprising a multi-day supply of unit dosages of the composition as described herein, and instructions directing the administration of said multi-day supply over a period of multiple days. In some embodiments, the kit comprises at least four unit dosages of the composition. In some embodiments, the kit comprises instructions for the dosing of said compositions, such as instructions directing the administration of at least 1, 2, 3, 4 or more unit dosages per day.

In another aspect, the invention provides a method for providing leucine and vitamin B6 supplementation to a subject, comprising: administering to the subject any of the compositions described herein. The composition can be a composition having a specified mass ratio of branched chain amino acids to vitamin B6, a composition having a synergistic effect, or a composition that is effective for regulating energy metabolism.

In some embodiments, the invention provides a method for maintaining and/or regulating energy metabolism in a subject comprising: administering to the subject any of the compositions described herein, wherein the energy metabolism of the subject is maintained and/or regulated over the time period. The composition can be a composition having a specified mass ratio of branched chain amino acids to vitamin B6, a composition having a synergistic effect, or a composition that is effective for regulating energy metabolism.

In other embodiments, the invention provides a method for reducing adipose volume and/or weight in a subject comprising: administering to the subject any of the compositions described herein for a time period effective to reduce adipose volume and/or weight in the subject by at least 5, 10, 15, or 20%. The composition can be a composition having a specified mass ratio of branched chain amino acids to vitamin B6, a composition having a synergistic effect, or a composition that is effective for regulating energy metabolism.

In one aspect, the invention provides methods for the administration of a combination composition as described herein. In some embodiments, the method comprises administering the composition to a subject in need thereof within an hour of the subject completing 15 minutes or more of moderate exercise (such as activity that elevates the subjects heart rate by at least 5%, 10%, 15%, 20%, 25%, 30%, or more above resting rate). In some embodiments, the method comprises administering the composition to a subject in need thereof at least two times per day.

In one aspect, the invention provides for a method for increasing energy metabolism in a subject in need thereof comprising administering a composition described herein, such as one comprising leucine and B6, to the subject for a time period in which the subject's energy metabolism is increased as compared to the energy metabolism in the subject prior to said time period.

In another aspect, the invention provides for a method for enhancing fat oxidation in a subject in need thereof comprising administering a composition described herein, such as one comprising leucine and/or a metabolite thereof and B6, at least two times per day over a time period, wherein the fat oxidation in the subject is increased over the time period as compared to the fat oxidation in the subject prior to said time period.

The invention also provides for a method for increasing energy metabolism in a subject comprising administering a composition described herein, such as one comprising leucine and/or a metabolite thereof and B6, at a selected dosing level, wherein the selected dosing level induces a circulating level of about 0.5 mM leucine and about 100 nM B6 in the subject.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawing(s) of which:

DETAILED DESCRIPTION OF THE INVENTION

Figure 1:
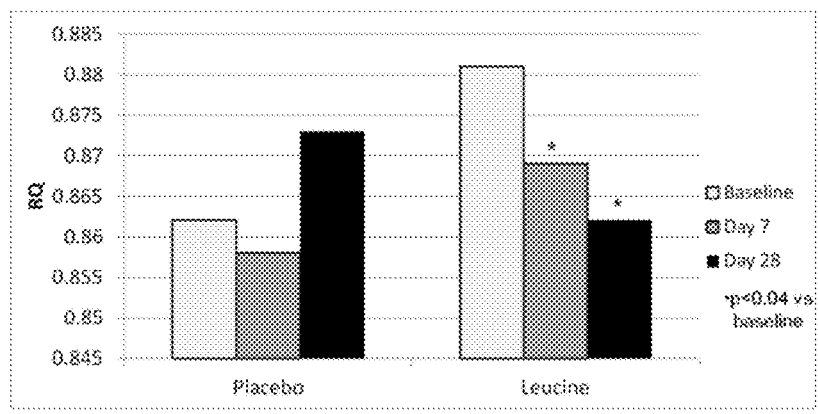
FIG. 1 depicts respiratory quotient for subjects administered a placebo composition and subjects administered a leucine-containing composition.

Several aspects of the invention are described below with reference to example applications for illustration. It should be understood that numerous specific details, relationships, and methods are set forth to provide a full understanding of the invention. One having ordinary skill in the relevant art, however, will readily recognize that the invention can be practiced without one or more of the specific details or with other methods. Unless stated otherwise, the present invention is not limited by the illustrated ordering of acts or events, as some acts may occur in different orders and/or concurrently with other acts or events. Furthermore, not all illustrated acts or events are required to implement a methodology in accordance with the present invention.

"Subject" refers to an animal, such as a mammal. The methods described herein can be useful in both human therapeutics, pre-clinical, and veterinary applications. In some embodiments, the subject is a mammal, and in some embodiments, the subject is human. Other mammals include, and are not limited to, apes, chimpanzees, orangutans, monkeys; domesticated animals (pets) such as dogs, cats, guinea pigs, hamsters, mice, rats, rabbits, and ferrets; domesticated farm animals such as cows, buffalo, bison, horses, donkey, swine, sheep, and goats; or exotic animals typically found in zoos, such as bear, lions, tigers, panthers, elephants, hippopotamus, rhinoceros, giraffes, antelopes, sloth, gazelles, zebras, wildebeests, prairie dogs, koala bears, kangaroo, pandas, giant pandas, hyena, seals, sea lions, and elephant seals.

The terms "administer", "administered", "administers" and "administering" are defined as the providing a composition to a subject via intravenous, intraarterial, oral, parenteral, buccal, topical, transdermal, rectal, intramuscular, subcutaneous, intraosseous, transmucosal, or intraperitoneal routes of administration. In certain embodiments of the subject application, oral routes of administering a composition may be preferred.

The term "effective amount" or "therapeutically effective amount" refers to that amount of an inhibitor described herein that is sufficient to effect the intended application including but not limited to disease treatment, as defined below. The therapeutically effective amount may vary depending upon the intended application (in vitro or in vivo), or the subject and disease condition being treated, e.g., the weight and age of the subject, the severity of the disease condition, the manner of administration and the like, which can readily be determined by one of ordinary skill in the art. The term also applies to a dose that will induce a particular response in target cells, e.g., reduction of proliferation or down regulation of activity of a target protein. The specific dose will vary depending on the particular compounds chosen, the dosing regimen to be followed, whether it is administered in combination with other compounds, timing of administration, the tissue to which it is administered, and the physical delivery system in which it is carried.

The term "energy metabolism," as used herein, refers to the transformation of energy that accompanies biochemical reactions in the body, including cellular metabolism and mitochondrial biogenesis. Energy metabolism can be quantified using the various measurements described herein, for example, weight-loss, fat-loss, insulin sensitivity, fatty acid oxidation, glucose utilization, triglyceride content, Sirt 1 expression level, AMPK expression level, oxidative stress, and mitochondrial biomass.

The term "substantially free," as used herein, refers to compositions that have less than about 10%, less than about 5%, less than about 1%, less than about 0.5%, less than 0.1% or even less of a specified component. For example a composition that is substantially free of non-branched chain amino acids may have less than about 1% of the non-branched chain amino acid lysine.

A "sub-therapeutic amount" of an agent or therapy is an amount less than the effective amount for that agent or therapy, but when combined with an effective or sub-therapeutic amount of another agent or therapy can produce a result desired by the physician, due to, for example, synergy in the resulting efficacious effects, or reduced side effects.

Compositions

The invention provides for compositions comprising combinations of branched chain amino acids and vitamin B6. Without being limited to any particular theory, these combinations described herein can promote energy partitioning from adipocytes to skeletal myotubes in co-culture systems, resulting in decreased energy storage in adipocytes and increased fatty acid utilization in muscle. In some embodiments, the composition of the present invention can inhibit adipocyte lipogenic gene expression and stimulate muscle fatty acid oxidation. These can be mediated, in part, by Sirt1-dependent stimulation of mitochondrial biogenesis and oxygen consumption. Moreover, adipocyte secreted factor(s) can suppress these effects, while leucine administration as described herein can permit a partial escape from this suppression. The combination of particular branched chain amino acids, or metabolites thereof, with vitamin B6 as detailed herein can offer nutritional and therapeutic benefits.

In some embodiments of the invention, the combination compositions can have a specified ratio of branched chain amino acids to vitamin B6. The specified ratio can provide for effective regulation of energy metabolism. For example, the specified ratios can cause a decrease in weight gain of a subject, a decrease in adipose volume of a subject, an increase in fat oxidation of a subject, an increase in insulin sensitivity of a subject, a decrease in oxidative stress markers of a subject, and/or a decrease in inflammatory markers of a subject. Such beneficial effects can result from, in part, an increase in mitochondrial biogenesis, or a variety of other changes in cellular metabolism or the energy metabolism pathway. The ratio of branched chain amino acids to vitamin B6 can be a mass ratio, a molar ratio, or a volume ratio. In some embodiments, the mass ratio of branched chain amino acids to vitamin B6 is about, greater than about, or less than about 45, 50, 55, 60, 65, 70, 75, 80, 85, 90, 100, 110, 120, 130, 140, 150, 175, 200, 250, 500, 750, 1000, or more. In other embodiments, the molar ratio of one or more branched chain amino acids to vitamin B6 contained in the subject compositions is about, greater than about, or less than about 90, 95, 90, 95, 100, 105, 110, 120, 130, 140, 150, 160, 170, 180, 190, 200, or more.

In some embodiments, the mass ratio of leucine to vitamin B6 in a unit dose is greater than about 65, 75, 85, or 95 and the amount of leucine in a unit dose is at least about 500, 750, 1000, 1125, or 1500 mg. As shown in Example 5, the effects of a combination composition of leucine and B6 can depend both on the ratio of leucine to B6 and the absolute level of leucine and B6. As described in Example 5, compositions that have a mass ratio greater than about 65 or 75, a leucine dosing of at least 500 or 1125 mg, and a B6 dosing of at least 5 or 15 mg can achieve a synergistic effect.

In some embodiments, the combination compositions are effective for regulating energy metabolism, as measured by a decrease in weight gain of a subject, a decrease in adipose volume of a subject, an increase in fat oxidation of a subject, an increase in insulin sensitivity of a subject, a decrease in oxidative stress markers of a subject, and/or a decrease in inflammatory markers of a subject. The administration of a combination composition can have a measured effect that is an improvement of about or greater than about 5, 10, 15, 20, 30, 50, 75, 100, 110, 120, 150, 200, 250, 350, 500, 700, or 1000% over a control subject or control group. For example, weight loss in a control group can be 1% of the initial average weight, whereas weight loss in a group administered a combination composition can be about 6% of the initial average weight of the group. The improvement can be 5%, or 500% of the weight loss in the control group. The weight loss can be observed within about 1 week, 2 weeks, 3, weeks, 4 weeks, 8 weeks, 12 weeks, 16 weeks, 24 weeks, 36 weeks, 52 weeks, or less. In some embodiments, weight loss is sustainable (i.e. weight lost is not regained) for a period of about 1 week, 2 weeks, 3 weeks, 4 weeks, 2 months, 4 months, 6 months, 1 year, or longer. In some embodiments, a subject taking a composition of the present invention exhibits weight loss of at least 0.05, 0.1, 0.5, 0.7, 1 kg, 2 kg, 5 kg, 10 kg, 20 kg or more over the course of the administration.

In other embodiments of the invention, a subject administered a composition described herein can experience a reduction in respiratory quotient. The reduction in respiratory quotient can be about, or greater than about 1, 5, 10, 15, 20, 25, 30, 35, or 40%, as compared to the subject's respiratory quotient before treatment. Alternatively the measurement of respiratory quotient can be for a test group as compared to a control group.

The effects on a subject, as described herein, can be determined by a variety of in vitro or in vivo methods that utilize samples taken from the subject or that directly assay for parameters indicative of the effect in the subject. For example, body weight can be measured on a calibrated scale, respiratory quotient can be measured using indirect calorimetry, insulin sensitivity can be measured using the homeostasis model of assessment of insulin resistance, oxidative stress can be measured using blood samples drawn from the subject, inflammatory markers can be measured using ELISA, fat mass or adipose tissue can be measured using X-ray absorptiometry.

Alternatively, the effects can be determined when myotubes or adipocytes are treated with a composition described herein. For example, myotubes or adipocytes can be treated with a composition and one or more effects on the myotubes or adipocytes can be measured. These measurements can include fatty acid oxidation, glucose utilization, Sirt1 expression, AMPK activation, and mitochondrial biomass. The compositions described herein can have an effect that increases fatty acid oxidation by at least about 50, 75, 100, 140, 150, 200, 300, 400, or 450% relative to untreated myotubes or adipocytes. The compositions described herein can have an effect that increases glucose utilization by at least about 50, 75, 100, 150, 200, or 300% relative to untreated myotubes or adipocytes. The compositions described herein can have an effect that increases glucose utilization by at least about 50, 75, 100, 150, 200, or 300% relative to untreated myotubes or adipocytes. The compositions described herein can have an effect that increases Sirt1 express or AMPK activation by at least 0.2, 0.5, 0.75, 1, 1.5, 2 or 3-fold relative to untreated myotubes or adipocytes.

In some embodiments the myotubes or adipocytes can be treated with media obtained from the other of the myotubes of adipocytes that were treated with the composition. For example, myotubes can be treated with media from adipocytes that were treated with the composition. Alternatively, adipocytes can be treated with media from myotubes that were treated with the composition.

The combination compositions, such as compositions with particular ratios of branched chain amino acids to vitamin B6, can also cause synergistic effects. These synergistic effects can be such that the one or more effects of the combination compositions are greater than the one or more effects of each component alone at a comparable dosing level, or they can be greater than the predicted sum of the effects of all of the components at a comparable dosing level, assuming that each component acts independently. The synergistic effect can be about, or greater than about 10, 20, 30, 50, 75, 100, 110, 120, 150, 200, 250, 350, or 500% better than the effect of treating a subject with one of the components alone, or the additive effects of each of the components when administered individually. The effect can be any of the measurable effects described herein. The composition comprising a plurality of components can be such that the synergistic effect is an enhancement in cellular metabolism, and that cellular metabolism is increased to a greater degree as compared to the sum of the effects of administering each component, determined as if each component exerted its effect independently, also referred to as the predicted additive effect herein. For example, if a composition comprising component (a) yields an effect of a 20% improvement in cellular metabolism and a composition comprising component (b) yields an effect of 50% improvement in cellular composition, then a composition comprising both component (a) and component (b) would have a synergistic effect if the combination composition's effect on cellular metabolism was greater than 70%.

A synergistic combination composition can have an effect that is greater than the predicted additive effect of administering each component of the combination composition alone as if each component exerted its effect independently. For example, if the predicted additive effect is 70%, an actual effect of 140% is 70% greater than the predicted additive effect or is 1 fold greater than the predicted additive effect. The synergistic effect can be at least about 20, 50, 75, 90, 100, 150, 200 or 300% greater than the predicted additive effect. Alternatively, the synergistic effect can be at least about 0.2, 0.5, 0.9, 1.1, 1.5, 1.7, 2, or 3 fold greater than the predicted additive effect.

In some embodiments, the synergistic effect of the combination compositions can also allow for reduced dosing amounts, leading to reduced side effects to the subject and reduced cost of treatment. Furthermore, the synergistic effect can allow for results that are not achievable through any other treatments. Therefore, proper identification, specification, and use of combination compositions can allow for significant improvements in the regulation of energy metabolism.

The combination compositions can further include one or more pharmaceutically active agents. Examples of therapeutically active agents include ibuprofen, aldoril, and gemfebrozil, verapamil, maxzide, diclofenac and metrolol, maproltiline, triazolam and minoxidil. For example, the combination compositions can comprise a pharmaceutically active anti-diabetic agent, weight loss agent, or calcium regulation agent. U.S. Pat. No. 7,109,198 and U.S. Patent Application No. 20090142336 describe a variety of pharmaceutically active agents or therapeutically active agents suitable for inclusion in a combination composition described herein. Examples of anti-diabetic agents include biguanides (such as metformin), thiazoladinediones and meglitinides (such as repaglinide, pioglitazone, and rosiglitazone), alpha glucosidease inhibitors (such as acarbose), sulfonylureas (such as tolbutamide, acetohexamide, tolazamide, chlorpropamide, glipizide, glyburide, glimepiride, gliclazide), incretins, ergot alkaloids (such as bromocriptine), and DPP inhibitors (such as sitagliptin, vildagliptin, saxagliptin, lingliptin, dutogliptin, gemigliptin, alogliptin, and berberine). The anti-diabetic agent can be an oral anti-diabetic agent. The anti-diabetic agent can also be injectable anti-diabetic drugs, including insulin, amylin analogues (such as pramlintide), and incretin mimetics (such as exenatide and liraglutide). Examples of anti-obesity therapeutic agents include lipase inhibitors (such as Orlistat), dopaminergic, noradrenergic, and serotoninergic compounds, cannabinoid receptor antagonists (such as rimonabant), exenatide, pramlintide, and CNS agents (such as topimerate). These examples are provided for discussion purposes only, and are intended to demonstrate the broad scope of applicability of the invention to a wide variety of drugs. It is not meant to limit the scope of the invention in any way.

The amount of pharmaceutical agent, or any other component used in a combination composition described herein, can be a used in an amount that is sub-therapeutic. Using sub-therapeutic amounts of an agent or component can reduce the side-effects of the agent. Use of sub-therapeutic amounts can be effective, particularly when used in synergy with other agents or components.

The sub-therapeutic amount of the agent or component can be such that it is an amount below which would be considered therapeutic. For example, FDA guidelines can suggest a specified level of dosing to treat a particular condition, and a sub-therapeutic amount would be any level that is below the FDA suggested dosing level. The sub-therapeutic amount can be about 1, 5, 10, 15, 20, 25, 30, 35, 50, 75, 90, or 95% less than the amount that is considered to be a therapeutic amount. The therapeutic amount can be assessed for individual subjects, or for groups of subjects. The group of subjects can be all potential subjects, or subjects having a particular characteristic such as age, weight, race, gender, or physical activity level.

In the case of metformin hydrochloride, the starting dose is 1000 mg daily, with subject specific dosing having a range of 500 mg to a maximum of 2500 mg daily (metformin hydrochloride extended-release tablets label http://www.accessdata.fda.gov/drugsatfda_docs/label/2008/021574s010lbl.pdf). The particular dosing for a subject can be determined by a clinician by titrating the dose and measuring the therapeutic response. The therapeutic dosing level can be determined by measuring fasting plasma glucose levels and measuring glycosylated hemoglobin. A sub-therapeutic amount can be any level that would be below the recommended dosing of metformin. For example, if a subject's therapeutic dosing level is determined to be 700 mg daily, a dose of 600 mg would be a sub-therapeutic amount. Alternatively, a sub-therapeutic amount can be determined relative to a group of subjects rather than an individual subject. For example, if the average therapeutic amount of metformin for subjects with weights over 300 lbs is 2000 mg, then a sub-therapeutic amount can be any amount below 2000 mg. In some embodiments, the dosing can be recommended by a healthcare provider including, but not limited to a patients' physician, nurse, and pharmacist.

Branched Chain Amino Acids

The invention provides for compositions that include branched chain amino acids. Branched chain amino acids can have aliphatic side chains with a branch carbon atom that is bound to two or more other atoms. The other atoms may be carbon atoms. Examples of branched chain amino acids include leucine, isoleucine, and valine. Branched chain amino acids may also include other compounds, such as 4-hydroxyisoleucine. In some embodiments, the compositions may be substantially free of one or more, or all of non-branched chain amino acids. For example, the compositions can be free of alanine, arginine, asparagine, aspartic acid, cysteine, glutamic acid, glutamine, glycine, histidine, lysine, methionine, phenylalanine, proline, serine, threonine, tryptophan, and/or tyrosine.

Without being limited to theory, ingestion of branched chain amino acids, such as leucine, can stimulate tissue protein synthesis via both mTOR-dependent and -independent pathways, as well as to exert an antiproteolytic effect. These effects predominate in muscle, but also can manifest in other tissues, including adipose tissue. Given the energetic cost of protein synthesis and turnover, leucine may increase fatty acid oxidation and net energy utilization and attenuate adiposity. Indeed, leucine has been reported to exert a thermogenic effect and to augment weight and adipose tissue loss during energy restriction. Also, leucine and leucine-rich diets to favorably modulate inflammatory cytokine patterns in adipocytes and mice.

In some embodiments, any of the compositions described herein can include salts, derivatives, metabolites, catabolites, anabolites, precursors, and analogs of any of the branched chain amino acids. For example, the metabolites of branched chain amino acids can include hydroxymethylbutyrate (HMB), α-hydroxyisocaproic acid, and keto-isocaproic acid (KIC), keto isovalerate, and keto antelisocaproate. Non-limiting exemplary anabolites of branched chain amino acids can include glutamate, glutamine, threonine, α-ketobytyrate, α-aceto-α-hydroxy butyrate, α,β-dihydroxy-β-methylvalerate, α-keto-β-methylvalerate, α,β-dihydroxy isovalerate, and α-keto isovalerate.

Vitamin B6

Without being limited to any particular theory or mode of action, elevations in the active B6 metabolite (pyridoxal phosphate) can reduce the tone and activity of the adipocyte calcium channel. Because intracellular free $Ca^{2+}$ is a primary regulator of adipocyte fatty acid synthase expression and activity, this results in a suppression of both the expression and activity of fatty acid synthase, which is one of the rate limiting steps in neutral lipid synthesis in adipocytes.

As used herein, vitamin B6 includes its different forms, including pyridoxine, pyridoxine 5'-phosphate, pyridoxal, pyridoxal phosphate, pyridoxal 5'-phosphate, pyridoxamine, pyridoxamine 5'-phosphate. In other embodiments, vitamin B6 can also include 4-pyridoxic acid, which is a catabolite of the above forms of vitamin B6 that is excreted. The compositions described herein can include any one or more of these forms of vitamin B6.

The active form of vitamin B6 in the body is pyridoxal 5-phosphate, which is a coenzyme for all transamination and some decarboxylation and deamination reactions. Furthermore, pyridoxal 5-phosphate is required as a coenzyme for all transamination reactions which occur in the body (Peterson D L, Martinez-Carrion M. The mechanism of transamination. Function of the histidyl residue at the active site of supernatant aspartate transaminase. J Biol Chem. 1970 Feb. 25; 245(4):806-13).

In some embodiments, any of the compositions described herein can include salts, derivatives, metabolites, catabolites, anabolites, precursors, and analogs of any of the forms of vitamin B6. Exemplary catabolites of vitamin B6 include 2-methyl-3-hydroxy-5-formylpyridine-4-carboxylate and 3-hydroxy-2-methylpyridine-4,5,-dicarboxylate. Exemplary analogs of vitamin B6 are described in U.S. Pat. Nos. 7,230,009, and 6,369,042. Exemplary precursors of vitamin B6 are described in U.S. Pat. No. 7,495,101.

Dosing Forms

The compositions described herein can be compounded into a variety of different dosage forms. It can be used orally as a tablet, chewable tablet, caplets, capsule, soft gelatin capsules, lozenges or solution. It can also be used as a nasal spray or for injection when in its solution form. In some embodiments, the composition may be a liquid composition suitable for oral consumption. Compositions of the invention suitable for oral administration can be presented as discrete dosage forms, such as capsules, cachets, or tablets, or liquids or aerosol sprays each containing a predetermined amount of an active ingredient as a powder or in granules, a solution, or a suspension in an aqueous or non-aqueous liquid, an oil-in-water emulsion, or a water-in-oil liquid emulsion, including liquid dosage forms (e.g., a suspension or slurry), and oral solid dosage forms (e.g., a tablet or bulk powder). Oral dosage forms may be formulated as tablets, pills, dragees, capsules, emulsions, lipophilic and hydrophilic suspensions, liquids, gels, syrups, slurries, suspensions and the like, for oral ingestion by an individual or a patient to be treated. Such dosage forms can be prepared by any of the methods of formulation. For example, the active ingredients can be brought into association with a carrier, which constitutes one or more necessary ingredients. Capsules suitable for oral administration include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. Optionally, the inventive composition for oral use can be obtained by mixing a composition a solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). In general, the compositions are prepared by uniformly and intimately admixing the active ingredient with liquid carriers or finely divided solid carriers or both, and then, if necessary, shaping the product into the desired presentation. For example, a tablet can be prepared by compression or molding, optionally with one or more accessory ingredients. Compressed tablets can be prepared by compressing in a suitable machine the active ingredient in a free-flowing form such as powder or granules, optionally mixed with an excipient such as, but not limited to, a binder, a lubricant, an inert diluent, and/or a surface active or dispersing agent. Molded tablets can be made by molding in a suitable machine a mixture of the powdered compound moistened with an inert liquid diluent.

The preparation of pharmaceutical compositions of this invention is conducted in accordance with generally accepted procedures for the preparation of pharmaceutical preparations. See, for example, Remington's Pharmaceutical Sciences 18th Edition (1990), E. W. Martin ed., Mack Publishing Co., PA. Depending on the intended use and mode of administration, it may be desirable to process the magnesium-counter ion compound further in the preparation of pharmaceutical compositions. Appropriate processing may include mixing with appropriate non-toxic and noninterfering components, sterilizing, dividing into dose units, and enclosing in a delivery device.

This invention further encompasses anhydrous compositions and dosage forms comprising an active ingredient, since water can facilitate the degradation of some compounds. For example, water may be added (e.g., 5%) in the arts as a means of simulating long-term storage in order to determine characteristics such as shelf-life or the stability of formulations over time. Anhydrous compositions and dosage forms of the invention can be prepared using anhydrous or low moisture containing ingredients and low moisture or low humidity conditions. Compositions and dosage forms of the invention which contain lactose can be made anhydrous if substantial contact with moisture and/or humidity during manufacturing, packaging, and/or storage is expected. An anhydrous composition may be prepared and stored such that its anhydrous nature is maintained. Accordingly, anhydrous compositions may be packaged using materials known to prevent exposure to water such that they can be included in suitable formulary kits. Examples of suitable packaging include, but are not limited to, hermetically sealed foils, plastic or the like, unit dose containers, blister packs, and strip packs.

A combination composition may comprise a branched chain amino acid, a B6 vitamin, and one or more additional ingredients. An additional ingredient may serve one or more functions. In some embodiments, an additional ingredient accounts for about, less than about, or more than about 0.1%, 0.5%, 1%, 2%, 3%, 4%, 5%, 6%, 7%, 8%, 9%, 10%, 15%, 20%, 25%, 30%, 40%, 50%, 60%, 70%, 80%, 90%, 95%, or more of the mass or volume of the combination composition. Non-limiting examples of additional ingredients include sweeteners, bulking agents, stabilizers, acidulants, preservatives, binders, lubricants, disintegrants, fillers, solubilizers, coloring agents (such as fruit juice and vegetable juice), and other additives and excipients known in the art. In some embodiments, a combination composition comprises one or more (e.g. 1, 2, 3, 4, 5, 6, 7, 8, 9, 10, 15, 20, or more) sweeteners. Examples of sweeteners include, but are not limited to, sucrose, fructose, dextrose, maltose, lactose, high fructose corn syrup solids, invert sugar, sugar alcohols, sorbitol, saccharin, cyclamates, sweeteners derived from *stevia*, sweeteners derived from *momordica grosvenorii*, sweeteners derived from mogrosides, acesulfame K, L-aspartyl-L-phenylalanine lower alkyl ester sweeteners, L-aspartyl-D-alanine amide sweeteners, L-aspartyl-D-serine amide sweeteners, L-aspartyl-L-1-hydroxymethylalkane-amide sweeteners, L-aspartyl-1-hydroxyethyalkaneamide sweeteners, L-aspartyl-D-phenylglycine ester and amide sweeteners, rebaudioside A, rebaudioside B, rebaudioside C, rebaudioside D, rebaudioside E, rebaudioside F, dulcoside A, dulcoside B, rubusoside, *stevia, stevia* extract, stevioside, mogroside IV, mogroside V, siamenoside, monatin and their salts (monatin SS, RR, RS, SR), curculin, glycyrrhizic acid and its salts, thaumatin, monellin, mabinlin, brazzein, hemandulcin, phyllodulcin, glycyphyllin, phloridzin, trilobatin, baiyunoside, osladin, polypodoside A, pterocaryoside A, pterocaryoside B, mukurozioside, phlomisoside I, periandrin I, abrusoside A, cyclocarioside I, sucralose, potassium acesulfame, aspartame, alitame, saccharin, neohesperidin dihydrochalcone, cyclamate, neotame, N—[N-[3-(3-hydroxy-4-methoxyphenyl)propyl]-L-α-aspartyl]L-phenylalanine-1-methyl ester, N—[N-[3-(3-hydroxy-4-methoxyphenyl)-3-methylbutyl]-L-α-aspartyl]-L-phenylalanine-1-methyl ester, N—[N-[3-(3-methoxy-4-hydroxyphenyl)propyl]-L-α-aspartyl]-L-phenylalanine-1-methyl ester, salts thereof, or combinations thereof. In some embodiments, the sweetener is a polyol additive, such as a sugar alcohol, erythritol, maltitol, mannitol, sorbitol, lactitol, xylitol, inositol, isomalt, propylene glycol, glycerol (glycerine), threitol, galactitol, palatinose, reduced isomalto-oligosaccharides, reduced xylo-oligosaccharides, reduced gentio-oligosaccharides, reduced maltose syrup, or reduced glucose syrup.

In some embodiments, a combination composition comprises one or more (e.g. 1, 2, 3, 4, 5, 6, 7, 8, 9, 10, 15, 20, or more) bulking agents. Non-limiting examples of bulking agents include guar gum, locust bean gum, *cassia* gum, pectin from botanical sources, high molecular weight carboxymethylcellulose, carrageenan, alginate, and xanthane. In some embodiments, one or more bulking agents may be added to enhance the viscosity of a liquid formulation.

In some embodiments, a combination composition comprises one or more (e.g. 1, 2, 3, 4, 5, 6, 7, 8, 9, 10, 15, 20, or more) stabilizers. Non-limiting examples of stabilizers include pectin, polysaccharide hydrolysates comprising dextrin, agar, can-ageenan, tamarind seed polysaccharides, *angelica* gum, karaya gum, xanthan gum, sodium alginate, tragacanth gum, guar gum, locust bean gum, pullulan, gellan gum, gum arabic, carboxymethylcellulose, and propylene glycol alginate ester. In some embodiments, one or more stabilizers are added to the combination composition to enhance the shelf-life of the combination composition. In general, shelf-life refers to the amount of time the container and composition therein can be held at ambient conditions (approximately room temperature, e.g. about 18-28° C.) or less, without degradation of the composition and/or container occurring to the extent that the composition cannot be used in the manner and for the purpose for which it was intended. In some embodiments, the combination composition has a shelf life of about, less than about, or more than about 1, 2, 3, 4, 5, 6, 7, 8, 9, 10, 11, 12, 14, 30, 60, 90, or more days; or about, less than about, or more than about 1, 2, 3, 4, 5, 6, 7, 8, 9, 10, 11, 12, or more months or years. In some embodiments, the combination composition remains non-perishable for a period of time after opening a container containing the composition. In general, perishability refers to degradation to an extent that the composition cannot be used in the manner and purpose for which it was designed. In some embodiments, the combination composition remains non-perishable for about, less than about, or more than about 1, 2, 3, 4, 5, 6, 7, 8, 9, 10, 11, 12, 18, 24, 30, 36, 48, 60, 72, 90, or more hours or days after opening; or about, less than about, or more than about 1, 2, 3, 4, 5, 6, 8, 10, 11, 12, or more months or years after opening. In some embodiments, the combination composition remains nonperishable for a period of time at room temperature (e.g. about 18-28° C.). In some embodiments, the combination composition remains non-perishable for a period of time upon refrigeration, such as storage below about 20° C., 15° C., 10° C., 5° C., 4° C., 3° C., 2° C., 1° C., 0° C., −1° C., −2° C., −3° C., −4° C., −5° C., −10° C., −20° C., or lower.

In some embodiments, a combination composition comprises one or more (e.g. 1, 2, 3, 4, 5, 6, 7, 8, 9, 10, 15, 20, or more) acidulants. Non-limiting examples of acidulants include C2-C30 carboxylic acids, substituted hydroxyl C1-C30 carboxylic acids, benzoic acid, substituted benzoic acids (e.g. 2,4-dihydroxybenzoic acid), substituted cinnamic acids, hydroxyacids, substituted hydroxybenzoic acids, substituted cyclohexyl carboxylic acids, tannic acid, lactic acid, tartaric acid, citric acid, gluconic acid, glucoheptonic acids, adipic acid, hydroxycitric acid, malic acid, fruitaric acid (a blend of malic, fumaric, and tartaric acids), fimaric acid, maleic acid, succinic acid, chlorogenic acid, salicylic acid, creatine, glucosamine hydrochloride, glucono delta lactone, caffeic acid, bile acids, acetic acid, ascorbic acid, alginic acid, erythorbic acid, polyglutamic acid, and their alkali or alkaline earth metal salt derivatives thereof.

In some embodiments, a combination composition comprises one or more (e.g. 1, 2, 3, 4, 5, 6, 7, 8, 9, 10, 15, 20, or more) preservatives. Non-limiting examples of preservatives include sorbic acid, benzoic acid, and salts thereof, including (but not limited to) calcium sorbate, sodium sorbate, potassium sorbate, calcium benzoate, sodium benzoate, potassium benzoate, and mixtures thereof.

An ingredient described herein can be combined in an intimate admixture with a pharmaceutical carrier according to conventional pharmaceutical compounding techniques. The carrier can take a wide variety of forms depending on the form of preparation desired for administration. In preparing the compositions for an oral dosage form, any of the usual pharmaceutical media can be employed as carriers, such as, for example, water, glycols, oils, alcohols, flavoring agents, preservatives, coloring agents, and the like in the case of oral liquid preparations (such as suspensions, solutions, and elixirs) or aerosols; or carriers such as starches, sugars, micro-crystalline cellulose, diluents, granulating agents, lubricants, binders, and disintegrating agents can be used in the case of oral solid preparations, in some embodiments without employing the use of lactose. For example, suitable carriers include powders, capsules, and tablets, with the solid oral preparations. If desired, tablets can be coated by standard aqueous or nonaqueous techniques.

Binders suitable for use in dosage forms include, but are not limited to, corn starch, potato starch, or other starches, gelatin, natural and synthetic gums such as acacia, sodium alginate, alginic acid, other alginates, powdered tragacanth, guar gum, cellulose and its derivatives (e.g., ethyl cellulose, cellulose acetate, carboxymethyl cellulose calcium, sodium carboxymethyl cellulose), polyvinyl pyrrolidone, methyl cellulose, pre-gelatinized starch, hydroxypropyl methyl cellulose, microcrystalline cellulose, and mixtures thereof.

Lubricants which can be used to form compositions and dosage forms of the invention include, but are not limited to, calcium stearate, magnesium stearate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil, and soybean oil), zinc stearate, ethyl oleate, ethylaureate, agar, or mixtures thereof. Additional lubricants include, for example, a syloid silica gel, a coagulated aerosol of synthetic silica, or mixtures thereof. A lubricant can optionally be added, in an amount of less than about 1 weight percent of the composition.

Lubricants can be also be used in conjunction with tissue barriers which include, but are not limited to, polysaccharides, polyglycans, seprafilm, interceed and hyaluronic acid.

Disintegrants may be used in the compositions of the invention to provide tablets that disintegrate when exposed to an aqueous environment. Too much of a disintegrant may produce tablets which may disintegrate in the bottle. Too little may be insufficient for disintegration to occur and may thus alter the rate and extent of release of the active ingredient(s) from the dosage form. Thus, a sufficient amount of disintegrant that is neither too little nor too much to detrimentally alter the release of the active ingredient(s) may be used to form the dosage forms of the compounds disclosed herein. The amount of disintegrant used may vary based upon the type of formulation and mode of administration, and may be readily discernible to those of ordinary skill in the art. About 0.5 to about 15 weight percent of disintegrant, or about 1 to about 5 weight percent of disintegrant, may be used in the pharmaceutical composition. Disintegrants that can be used to form compositions and dosage forms of the invention include, but are not limited to, agar-agar, alginic acid, calcium carbonate, microcrystalline cellulose, croscarmellose sodium, crospovidone, polacrilin potassium, sodium starch glycolate, potato or tapioca starch, other starches, pre-gelatinized starch, other starches, clays, other algins, other celluloses, gums or mixtures thereof.

Examples of suitable fillers for use in the compositions and dosage forms disclosed herein include, but are not limited to, talc, calcium carbonate (e.g., granules or powder), microcrystalline cellulose, powdered cellulose, dextrates, kaolin, mannitol, silicic acid, sorbitol, starch, pre-gelatinized starch, and mixtures thereof.

When aqueous suspensions and/or elixirs are desired for oral administration, the active ingredient therein may be combined with various sweetening or flavoring agents, coloring matter or dyes and, if so desired, emulsifying and/or suspending agents, together with such diluents as water, ethanol, propylene glycol, glycerin and various combinations thereof.

The tablets can be uncoated or coated by known techniques to delay disintegration and absorption in the gastrointestinal tract and thereby provide a sustained action over a longer period. For example, a time delay material such as glyceryl monostearate or glyceryl distearate can be employed. Formulations for oral use can also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example, peanut oil, liquid paraffin or olive oil.

In one embodiment, the composition may include a solubilizer to ensure good solubilization and/or dissolution of the compound of the present invention and to minimize precipitation of the compound of the present invention. This can be especially important for compositions for non-oral use, e.g., compositions for injection. A solubilizer may also be added to increase the solubility of the hydrophilic drug and/or other components, such as surfactants, or to maintain the composition as a stable or homogeneous solution or dispersion.

The composition can further include one or more pharmaceutically acceptable additives and excipients. Such additives and excipients include, without limitation, detackifiers, anti-foaming agents, buffering agents, polymers, antioxidants, preservatives, chelating agents, viscomodulators, tonicifiers, flavorants, colorants, odorants, opacifiers, suspending agents, binders, fillers, plasticizers, lubricants, and mixtures thereof. A non-exhaustive list of examples of excipients includes monoglycerides, magnesium stearate, modified food starch, gelatin, microcrystalline cellulose, glycerin, stearic acid, silica, yellow beeswax, lecithin, hydroxypropylcellulose, croscarmellose sodium, and crospovidone.

The compositions described herein can also be formulated as extended-release, sustained-release or time-release such that one or more components are released over time. Delayed release can be achieved by formulating the one or more components in a matrix of a variety of materials or by microencapsulation. The compositions can be formulated to release one or more components over a time period of 4, 6, 8, 12, 16, 20, or 24 hours. The release of the one or more components can be at a constant or changing rate.

In some embodiments, the compositions can be formulated in a food composition. For example, the compositions can be a beverage or other liquids, solid food, semi-solid food, with or without a food carrier. For example, the compositions can include a black tea supplemented with leucine and vitamin B6 according to the present invention. The composition can be a dairy product supplemented with leucine and vitamins B6 according to the present invention. In some embodiments, the compositions can be formulated in a food composition. For example, the compositions can comprise a beverage, solid food, semi-solid food, or a food carrier. For example, the compositions can include a black tea supplemented with leucine and vitamin B6. In some embodiments, the combination composition is packaged in a container (e.g. a bottle) as a liquid suspension for oral consumption, such as a beverage. In some embodiments, each container constitutes a unit dose. In some embodiments, the volume of the liquid suspension is about, less than about, or more than about 5 mL, 10 mL, 15 mL, 20 mL, 15 mL, 30 mL, 60 mL, 90 mL, 120 mL, 240 mL, 500 mL, 600 mL, 700 mL, 800 mL, 900 mL, 1000 mL, or more. In some embodiments, the volume of the liquid suspension is about, less than about, or more than about 0.5 oz, 1 oz, 2 oz, 3 oz, 4 oz, 5 oz, 6 oz, 7 oz, 8 oz, 9 oz, 10 oz, 11 oz, 12 oz, 16 oz, 18 oz, 20 oz, 24 oz, 30 oz, 36 oz, 48 oz, or more. In some embodiments, the combination composition comprises the characteristics listed in Table 1.

TABLE 1

Branched chain amino acid (about 500 mg to 2200 mg)
Vitamin B6 (about 5 mg to 30 mg)
Sugar (about 0.1 g to 10 g)
Sugar alcohol (about 0.1 to 10 g)
Bulking agent (about 10 mg to 2000 mg)
Stabilizer (about 10 mg to 2000 mg)
Other sweeteners (about 10 mg to 2000 mg)
Acidulants (about 10 mg to 2000 mg)
Preservatives (about 10 mg to 2000 mg)
Total Volume of about 5 mL to 1 L (e.g. 2 oz)
Shelf-life of more than about 7 months Alternatively, the compositions can be a snack bar supplemented with leucine and vitamin B6. For example, the snack bar can be a chocolate bar, a granola bar, or a trail mix bar. In yet another embodiment, the present dietary supplement or food compositions are formulated to have suitable and desirable taste, texture, and viscosity for consumption. Any suitable food carrier can be used in the present food compositions. Food carriers of the present invention include practically any food product. Examples of such food carriers include, but are not limited to food bars (granola bars, protein bars, candy bars, etc.), cereal products (oatmeal, breakfast cereals, granola, etc.), bakery products (bread, donuts, crackers, bagels, pastries, cakes, etc.), beverages (milk-based beverage, sports drinks, fruit juices, alcoholic beverages, bottled waters), pastas, grains (rice, corn, oats, rye, wheat, flour, etc.), egg products, snacks (candy, chips, gum, chocolate, etc.), meats, fruits, and vegetables. In an embodiment, food carriers employed herein can mask the undesirable taste (e.g., bitterness). Where desired, the food composition presented herein exhibit more desirable textures and aromas than that of any of the components described herein. For example, liquid food carriers may be used according to the invention to obtain the present food compositions in the form of beverages, such as supplemented juices, coffees, teas, and the like. In other embodiments, solid food carriers may be used according to the invention to obtain the present food compositions in the form of meal replacements, such as supplemented snack bars, pasta, breads, and the like. In yet other embodiments, semi-solid food carriers may be used according to the invention to obtain the present food compositions in the form of gums, chewy candies or snacks, and the like.

The dosing of the combination compositions can be about, less than about, or more than about 1, 2, 3, 4, 5, 6, 7, 8, 9, 10 or more times a daily. A subject can receive dosing for a period of about, less than about, or greater than about 1, 2, 3, 4, 5, 6, 7, 8, 9, 10, 11, 12, 13, 14 or more days, weeks or months. A unit dose can be chosen such that the subject is administered about or greater than about 1000 mg of branched chain amino acids (e.g. about or more than about 1100 mg, 1130 mg, 2000 mg, 2100 mg, 2200 mg, 2250 mg, 2260 mg, 3300 mg, 3390 mg, 4400 mg, 4520 mg, or more) and about or greater than about 10 mg of vitamin B6 (e.g. 11 mg, 12 mg, 13 mg, 14 mg, 15 mg, 16 mg, 17 mg, 18 mg, 19 mg, 20 mg, 24 mg, 30 mg, 36 mg, 45 mg, 48 mg, 60 mg, or more) daily. The branched chain amino acids can comprise leucine. A unit dose can be a fraction of the daily dose, such as the daily dose divided by the number of unit doses to be administered per day. A unit dose can be a fraction of the daily dose that is the daily dose divided by the number of unit doses to be administered per day and further divided by the number of unit doses (e.g. tablets) per administration. The number of unit doses per administration may be about, less than about, or more than about 1, 2, 3, 4, 5, 6, 7, 8, 9, 10, or more. The number of doses per day may be about, less than about, or more than about 1, 2, 3, 4, 5, 6, 7, 8, 9, 10, or more. The number of unit doses per day may be determined by dividing the daily dose by the unit dose, and may be about, less than about, or more than about 1, 2, 3, 4, 5, 6, 7, 8, 9, 10, 11, 12, 13, 14, 15, 6, 17, 18, 19, 20, or more unit doses per day. For example, a unit dose can be about ½, ⅓, ¼, ⅕, ⅙, ⅐, ⅛, ⅑, ⅒. A unit dose can be about one-third of the daily amount and administered to the subject three times daily. A unit dose can be about one-half of the daily amount and administered to the subject twice daily. A unit dose can be about one-fourth of the daily amount with two unit doses administered to the subject twice daily. For example, a unit dose can have about, less than about, or more than about 250 mg, 275 mg, 500 mg, 550 mg, 750 mg, 825 mg, 1100 mg, 1125 mg, 1130 mg, 1650 mg, 2200 mg, or more of leucine and about, less than about, or more than about 3.75 mg, 7.5 mg, 10 mg, 11.25 mg, 15 mg, or more of vitamin B6.

In some embodiments, the dosing of leucine, any metabolites of leucine, and/or vitamin B6 can be designed to achieve a specified physiological concentration or circulating level of leucine, metabolites of leucine and/or vitamin B6. The physiological concentration can be a circulating level as measured in the blood stream of a subject. The subject can be a human or an animal. A selected dosing can be altered based on the characteristics of the subject, such as weight, rate of energy metabolism, genetics, ethnicity, height, or any other characteristic. The amount of leucine in a unit dose can be such that the circulating level of leucine in a subject is about or greater than about 0.25 mM, 0.5 mM, 0.75 mM, or 1 mM. A dosing of about 1,125 mg leucine can achieve a circulating level of leucine in a subject that is about 0.5 mM. A dosing of about 300 mg leucine can achieve a circulating level of leucine in a subject that is about 0.25 mM. A dosing of about 15 mg of vitamin B6 can achieve a circulating level of vitamin B6 that is about 100 nM. A dosing of about 7.5 mg of vitamin B6 can achieve a circulating level of vitamin B6 that is about 50 nM. The amount of vitamin B6 in a unit dose can be such that the circulating level of vitamin B6 in a subject is about or greater than about 10, 25, 50, 100, 150, or 200 nM. The amount of leucine and vitamin B6 in a unit dose can be such that the circulating level of leucine in a subject is about 0.5 mM and the circulating level of vitamin B6 in the subject is about 100 nM.

Methods

The invention provides for methods of regulating energy metabolism by administering one or more compositions. These compositions include the combination compositions described herein, such as combination compositions comprising branched chain amino acids and vitamin B6. The combination compositions can be formulated for oral administration in the form of a tablet, a capsule, or any other form described herein.

The compositions can be administered to a subject orally or by any other methods. Methods of oral administration include administering the composition as a liquid, a solid, or a semi-solid that can be taken in the form of a dietary supplement or a food stuff.

The compositions can be administered periodically. For example, the compositions can be administered one, two, three, four times a day, or even more frequent. The subject can be administered every 1, 2, 3, 4, 5, 6 or 7 days. In some embodiments, the compositions are administered three times daily. The administration can be concurrent with meal time of a subject. The period of treatment or diet supplementation can be for about 1, 2, 3, 4, 5, 6, 7, 8, or 9 days, 2 weeks, 1-11 months, or 1 year, 2 years, 5 years or even longer. In some embodiments of the invention, the dosages that are administered to a subject can change or remain constant over the period of treatment. For example, the daily dosing amounts can increase or decrease over the period of administration.

The compositions can be administered to a subject such that the subject is administered a selected total daily dose of the composition. The total daily dose can be determined by the sum of doses administered over a 24 hour period. The total daily dose of the composition can include at least about 250, 500, 750, 1000, 1125, 2000, 2250 mg or more of a branched chain amino acid or metabolite thereof. The branched chain amino acid can be leucine, HMB, or any other branched chain amino acid described herein. The total daily dose of the composition can include at least about 3, 7.5, 15, 30, 45, 90 mg or more of B6. The total daily dose of the composition can have a mass ratio of branched chain amino acids or metabolite thereof to vitamin B6 that is about, greater than about, or less than about 45, 50, 55, 60, 65, 70, 75, 80, 85, 90, 100, 110, 120, 130, 140, 150, 175, 200, 250, 500, 750, 1000, or more.

In some embodiments, a selected dose of a composition can be administered to a subject such that the subject achieves a desired circulating level of the composition. The desired circulating level of the composition can be at least about 0.25, 0.5, 0.75, 1 mM or more of leucine. The desired circulating level of the composition can be at least about 10, 25, 50, 100, 150, or 200 nM or more of B6. The selected dose can be chosen based on the characteristics of the subject, such as weight, height, ethnicity, or genetics.

In another aspect, the invention provides for a method for increasing energy metabolism in a subject, comprising administering a composition described herein, such as one comprising leucine and B6, to a subject in need for a period of time in which the subject's energy metabolism is increased. The invention also provides for a method for enhancing fat oxidation in a subject in need thereof comprising administering a composition described herein at least two times per day over a time period, wherein the fat oxidation in the subject is increased over the time period as compared to the fat oxidation in the subject prior to said time period. The subject's energy metabolism can be measured before treatment and after treatment to determine if the subject's energy metabolism has increased. Alternatively, subjects can be pooled into test and control groups, where the increase in energy metabolism is measured between groups.

The length of the period of administration and/or the dosing amounts can be determined by a physician, a nutritionist, or any other type of clinician. The period of time can be one, two, three, four or more weeks. Alternatively, the period of time can be one, two, three, four, five, six or more months.

In another aspect, the invention provides for a method for increasing energy metabolism in a subject comprising administering a composition described herein at a selected dosing level, wherein the selected dosing level induces a circulating level of about 0.5 mM leucine and about 100 nM B6 in the subject. The dosing level can be adjusted based on the subject's characteristics, such as weight, height, ethnicity, genetics, or baseline energy metabolism level.

The physician, nutritionist, or clinician can observe the subject's response to the administered compositions and adjust the dosing based on the subject's performance or measured circulating levels of leucine, B6, or any other component of the composition. For example, dosing levels can be increased for subjects that show reduced effects in energy regulation or circulating levels of B6 or Leucine below desired target levels.

In some embodiments, the compositions administered to a subject can be optimized for a given subject. For example, the ratio of branched chain amino acids to vitamin B6 or the particular components in a combination composition can be adjusted. The ratio and/or particular components can be selected after evaluation of the subject after being administered one or more compositions with varying ratios of branched chain amino acids to vitamin B6 or varying combination composition components.

The administration of a composition described herein, such as a combination composition, to a subject can allow for the regulation or maintenance of the subject's energy metabolism. The regulation or maintenance of energy metabolism can allow for a subject to experience a number of beneficial effects. These beneficial effects include a reduction in weight, a reduction in adipose tissue, an increase in fatty acid oxidation, an increase in insulin sensitivity, a decrease in oxidative stress, and/or a decrease in inflammation. Compared to a baseline prior to treatment, these effects can result in an improvement of about or greater than about 5, 10, 15, 20, 30, 40, 50, 75, 100, 125, 150, 200, 250, 300, 400, or 500%. Alternatively, administration of a composition described herein can allow for maintenance of the subject's weight, amount of adipose tissue, amount of fatty acid oxidation, level of insulin sensitivity, oxidative stress level, and/or level of inflammation. These amounts and/or levels can be maintained within 0, 1, 5, or 10% of the amounts and/or levels at the initiation of administration.

Kits

The invention also provides kits. The kits include one or more compositions described herein, in suitable packaging, and may further comprise written material that can include instructions for use, discussion of clinical studies, listing of side effects, and the like. Such kits may also include information, such as scientific literature references, package insert materials, clinical trial results, and/or summaries of these and the like, which indicate or establish the activities and/or advantages of the composition, and/or which describe dosing, administration, side effects, drug interactions, or other information useful to the health care provider. Such information may be based on the results of various studies, for example, studies using experimental animals involving in vivo models and studies based on human clinical trials. A kit may comprise one or more unit doses described herein. In some embodiments, a kit comprises about, less than about, or more than about 1, 2, 3, 4, 5, 6, 7, 8, 9, 10, 11, 12, 13, 14, 15, 16, 17, 18, 19, 20, 30, 31, 60, 90, 120, 150, 180, 210, or more unit doses. Instructions for use can comprise dosing instructions, such as instructions to take 1, 2, 3, 4, 5, 6, 7, 8, 9, 10, or more unit doses 1, 2, 3, 4, 5, 6, 7, 8, 9, 10, or more times per day. For example, a kit may comprise a unit dose supplied as a tablet, with each tablet package separately, multiples of tablets packaged separately according to the number of unit doses per administration (e.g. pairs of tablets), or all tablets packaged together (e.g. in a bottle). As a further example, a kit may comprise a unit dose supplied as a bottled drink, the kit comprising 1, 2, 3, 4, 5, 6, 7, 8, 9, 10, 11, 12, 13, 14, 24, 28, 36, 48, 72, or more bottles.

The kit may further contain another agent. In some embodiments, the compound of the present invention and the agent are provided as separate compositions in separate containers within the kit. In some embodiments, the compound of the present invention and the agent are provided as a single composition within a container in the kit. Suitable packaging and additional articles for use (e.g., measuring cup for liquid preparations, foil wrapping to minimize exposure to air, and the like) are known in the art and may be included in the kit. Kits described herein can be provided, marketed and/or promoted to health providers, including physicians, nurses, pharmacists, formulary officials, and the like. Kits may also, in some embodiments, be marketed directly to the consumer.

In some embodiments, a kit can comprise a multi-day supply of unit dosages. The unit dosages can be any unit dosage described herein. The kit can comprise instructions directing the administration of the multi-day supply of unit dosages over a period of multiple days. The multi-day supply can be a one-month supply, a 30-day supply, or a multi-week supply. The multi-day supply can be a 90-day, 180-day, 3-month or 6-month supply. The kit can include packaged daily unit dosages, such as packages of 1, 2, 3, 4, or 5 unit dosages. The kit can be packaged with other dietary supplements, vitamins, and meal replacement bars, mixes, and beverages.

EXAMPLES

Example 1

Effects on Fat Oxidation, and Oxidative and Inflammatory Stress in Overweight and Obese Subjects Twenty overweight and obese subjects (11 males, 9 females aged 29+4.5 years, BMI 31.2±2.4) were randomized to receive a blend comprising leucine and pyridoxal phosphate (760 mg total, 750 mg leucine, 10 mg pyrodixal phosphate) or placebo three times/day in the presence of their usual diet, activity and tobacco use patterns for four weeks. All subjects were weight stable for the four weeks preceding study initiation, and met the following exclusion criteria: significant endocrine, metabolic or gastrointestinal disease; obesity pharmacotherapy (prescription or OTC) within preceding four weeks; pregnancy or lactation; recent (past four weeks) initiating or change in diet or exercise program; recent (past four weeks) change in pattern of tobacco use; recent (past 12 weeks) use of psychotropic medications.

The blend was added to black tea, and unsupplemented black tea served as the placebo. All subjects were provided individual instruction, counseling and assessment from the study staff regarding maintaining usual patterns of diet, activity and tobacco use. Physical activity was assessed using pedometer counts and maintained at approximately pre-study levels throughout the study. Subjects were instructed to maintain a constant level of activity (plus or minus 500 steps/day) and used pedometers for self-assessment. Pedometer counts were recorded and provided to the study staff on a weekly basis, along with the diet, physical activity and tobacco records maintained in diaries provided. Weight and height were measured upon study entry for purposes of calculating body mass index.

Measurements:

Anthropometric Measurements: Body weight was measured with a calibrated scale and height measured with a wall-mounted stadiometer, and body mass index was calculated via standard equation ($kg/m^2$).

Resting metabolic rate (RMR)/Substrate Oxidation: RMR and respiratory quotient (RQ) were assessed at baseline and days 7 and 28. Respiratory gas exchange was measured by indirect calorimetry using the open circuit technique between the hours of 6 AM and 10 AM after a 12-hour fast and 48-hour abstention from exercise; a SensorMedics Vmax 29n metabolic cart (Sensor Medics, Anaheim, Calif.). was used for all measurements. Following a urinary void, the participant rested quietly for 30 minutes in an isolated room with temperature controlled (21-24° C.) environment. The subject was then placed in a ventilated hood for a minimum of 30 minutes, until steady state was achieved. Criteria for a valid measurement was a minimum of 15 minutes of steady state, with steady state determined as less than 10% fluctuation in minute ventilation and oxygen consumption and less than 5% fluctuation in respiratory quotient. Metabolic rate was calculated using the Weir equation, RQ was calculated as $CO_2$ production/$O_2$ consumption, and substrate oxidation was calculated from RQ after correction for urinary nitrogen losses.

$HOMA_{IR}$: The homeostasis model assessment of insulin resistance ($HOMA_{IR}$) was used as a screening index of changes in insulin sensitivity. $HOMA_{IR}$ is calculated via standard formula from fasting plasma insulin and glucose as follows: $HOMA_{IR}$=[Insulin (uU/mL)×glucose (mM)]/22.5.

ROS/Oxidative Stress: Blood was drawn into EDTA-treated tubes, centrifuged to separate plasma, and samples aliquoted for individual assays; plasma was maintained at −80° C. under nitrogen to prevent oxidative changes prior to measurements. Plasma malonaldehyde (MDA) was measured using a fluorometric assay, and plasma 8-isoprostane $F_{2\alpha}$ was measured by ELISA (Assay Designs, Ann Arbor, Mich.).

Inflammatory Markers and Cytokines: IL-6, adiponectin, TNF-α and CRP levels in plasma were determined by ELISA (Assay Designs, Ann Arbor, Mich.; Linco Research, St. Charles, Mo.; and Bioscience, San Diego, Calif.).

Statistical Analysis: Change from baseline values were computed for every outcome variable. These data were analyzed using a multivariate analysis of variance (MANOVA), simultaneously testing the null hypothesis that the means for each outcome variable are equal across treatments. The MANOVA was conducted to test for the main effects of treatment (NuFit vs. placebo), and gender and the possible interaction among these main effects. Potential adjustments for baseline BMI was assessed in the model, but was not significant. SAS-PC was used for all analyses.

Results

Figure 2:
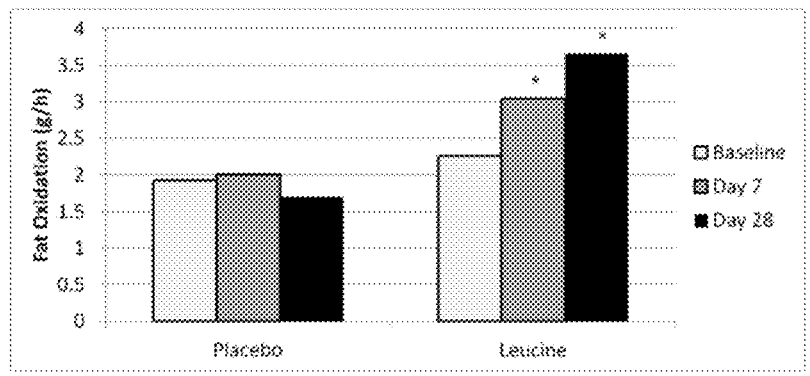
FIG. 2 depicts fat oxidation in subjects administered a placebo composition and subjects administered a leucine-containing composition.

The blend supplement of leucine and vitamin B6 according to the present invention resulted in a significant decrease in RQ, with a corresponding increase in fat oxidation by day 7, with further increases from day 7 to day 28, as shown in FIG. 1. One exemplary composition tested herein comprises (namely NuFit) 750 mg leucine and 10 mg pyridoxal phosphate (administered three times daily). RQ decreased by 0.019 units (p<0.04), and fat oxidation increased by 1.4+0.4 g/hour, or 33.6 g/day, as shown in FIG. 2, while no significant effects were found in the placebo group. This shows that the fat oxidation can be increased by about 60% over the initial fat oxidation rate for subjects administered NuFit.

Figure 3:
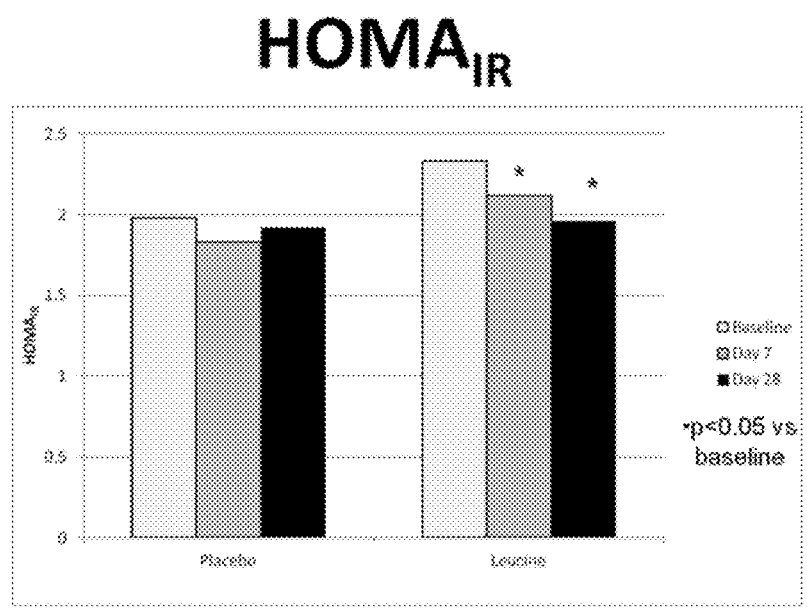
FIG. 3 depicts homeostasis model assessment of insulin resistance in subjects administered a placebo composition and subjects administered a leucine-containing composition.

Although there was no significant treatment effect on plasma glucose or lipids, insulin sensitivity, as measured by $HOMA_{IR}$ was significantly improved in the blend-supplemented group, while the placebo group did not change significantly, as shown in FIG. 3.

The blend supplement resulted in a significant decrease in oxidative stress, as demonstrated by a 20% reduction in plasma MDA (from 4.0+0.2 to 3.2+0.3 nmol/L, p<0.01) and a 17% decrease in plasma 8-isoprostane-F2α (from 44.1+3 to 36.6+3 pg/mL, p<0.005). Inflammatory stress biomarkers exhibited similar improvements with blend treatment, while no significant effects were found in the placebo group. TNF-α exhibited a 15% decrease, from 393+29 to 334+38 pg/mL, while C-reactive protein exhibited a 38% decrease, from 36.8+7.4 to 22.8+8.3 µg/mL, p<0.01). Consistent with these findings, the adipocyte-derived anti-inflammatory biomarker adiponectin exhibited a 67% increase (from 9.6+1.4 to 15.6+2.3 ng/mL, p<0.001). This finding is consistent with the observed improvements in insulin sensitivity and fat oxidation, as adiponectin can stimulate fat oxidation in liver and skeletal muscle and augment insulin signaling in adipose tissue and skeletal muscle.

Leucine treatment can alter energy partitioning between adipose tissue and skeletal muscle, resulting in reduced net lipid storage in adipose tissue and increased fat oxidation in muscle. Blends of leucine and pyridoxine are significantly more effective than leucine alone in regulating energy metabolism. These blends are also effective in improving insulin sensitivity, as measured using an index of insulin sensitivity ($HOMA_{IR}$). Here, we observed a 10-~15% reduction in insulin resistance. Another net effect of increased mitochondrial biogenesis is generally is a reduction in oxidative and inflammatory stress. Furthermore, compositions comprising leucine and pyridoxine (e.g. vitamin B6) can also favorably modulate inflammatory cytokine patterns.

Blends containing leucine (2.25 g/day) and pyridoxine (30 mg/day) effectively increase fat oxidation and improve insulin sensitivity in overweight and obese subjects. Moreover, the blend significantly attenuates the oxidative and inflammatory stress which otherwise associated with both obesity and insulin resistance and which are closely associated with major obesity-associated co-morbidities. Accordingly, this supplement provides a useful aid in the management of obesity and associated co-morbidities and can be, by virtue of its effects on fat oxidation, a useful compound in healthy weight management/obesity prevention.

Example 2

Effects on Body Weight and Body Composition

Design

Placebo-controlled, parallel group double-blind randomized trial

Treatments: NuShape (1,125 mg leucine+15 mg vitamin B6) taken twice daily (total daily dosage=2250 mg leucine+30 mg B6) vs. placebo.

24 weeks

Experiment 1: Balanced deficit diet: −500 kcal/day from usual diet and from calculated maintenance energy needs. Macronutrient distribution matched to US (~35% of calories from fat, 15% from protein, 50% from carbohydrate)

Experiment 2: Eucaloric: Macronutrient distribution matched to US (~35% of calories from fat, 15% from protein, 50% from carbohydrate), as with Experiment 1

Outpatient, with weekly monitoring and visits.

Subjects

N=20 (Experiment 1), N=24 (Experiment 2). No differences in measured baseline characteristics between groups BMI=34.76±2.57 (Experiment 1), 35.92±2.85 (Experiment 2)

Age 26.82±4.24 (Experiment 1), 25.73±4.89 years (Experiment 2)

Gender: 14 Female, 6 male (Experiment 1), 12 female, 12 male (Experiment 2)

Measurements:

Body weight and fat (via dual energy x-ray absorptiometry (DEXA; Lunar Prodigy DXA, GE Lunar, Madison, Wis.) at baseline, 12 and 24 weeks.

Body weight was measured with a calibrated scale and height measured with a wall-mounted stadiometer, and body mass index was calculated via standard equation ($kg/m^2$).

Fat mass was assessed via dual-energy X-ray absorptiometry at baseline, and 12 and 24 weeks. A LUNAR Prodigy dual-energy X-ray absorptiometry system (GE Healthcare, Madison, Wis.) maintained and calibrated by LUNAR staff annually was used. A spine phantom was assessed every day to determine whether any drift in the machine occurred, followed by the daily calibration block; spine phantom variation was <3% throughout the study.

Results

Experiment 1:

| | 12 Weeks | 24 Weeks | Significance (placebo vs. NuShape) |
|---|---|---|---|
| Placebo-Weight Loss (kg) | 3.40 ± 0.81 | 5.25 ± 1.13 | |
| NuShape-Weight Loss (kg) | 6.18 ± 1.02 | 8.15 ± 1.33 | *p < 0.01 (12 and 24 weeks) |
| Placebo-Fat Loss (kg) | 2.31 ± 0.53 | 4.22 ± 0.74 | |
| NuShape-Fat Loss (kg) | 4.96 ± 0.61 | 7.00 ± 0.95 | *p < 0.01 (12 and 24 weeks) |

Experiment 2 (weight maintained by design):

| | 12 Weeks | 24 Weeks | Significance (placebo vs. NuShape) |
|---|---|---|---|
| Placebo-Fat Loss (kg) | −0.04 ± 0.51 | 0.02 ± 0.43 | |
| NuShape-Fat Loss (kg) | 1.12 ± 0.36 | 1.82 ± 0.70 | *p < 0.01 (12 and 24 weeks) |

As shown in Experiment 1, the subjects administered NuShape lost about 80% more weight at 12 weeks and 55% more weight at 24 weeks as compared to subjects administered a placebo. Additionally, subjects administered NuShape lost about 114% more fat at 12 weeks and 65% more fat at 24 weeks as compared to subjects administered a placebo.

Example 3

Interactive Effects of Pyridoxal Phosphate (PLP) and Leucine on Adipocyte Metabolism The leucine dosing of 0.5 mM used in these experiments is the level achieved in circulation following ingestion of the blend formula described herein. Similarly, the dose of pyridoxal phosphate (PLP, the active metabolite of B6; 100 nM) used in these experiments is the level achieved in circulation following ingestion of the blend formula described herein.

Methods

Cell culture: 3T3-L1 pre-adipocytes were incubated at a density of 8000 cells/cm$^2$ (10 cm$^2$ dish) and grown in the absence of insulin in Dulbecco's modified Eagle's medium (DMEM) containing 10% FBS and antibiotics (1% penicillin-streptomycin)(adipocyte medium) at 37° C. in 5% CO$_2$ in air. Confluent pre-adipocytes were induced to differentiate with a standard differentiation medium consisting of DMEM-F10 (1:1, vol/vol) medium supplemented with 1% fetal bovine serum (FBS), 250 nM dexamethasone (DEXA), isobutylmethylxanthine (IBMX) (0.5 mM) and antibiotics. Pre-adipocytes were maintained in this differentiation medium for 3 days (unless specifically indicated) and subsequently cultured in adipocyte medium. Cultures were re-fed every 2-3 days to allow 90% cells to reach fully differentiation before treatment.

Fatty acid synthase (FAS) mRNA expression: Adipocyte FAS and 18s were quantitatively measured using a smart cycler real-time PCR system (Cepheid, Sunnyvale, Calif.) with a TaqMan 1000 Core Reagent Kit (Applied Biosystems, Branchburg, N.J.). The primers and probe sets were obtained from Applied Biosystems TaqMan® Assays-on-Demand™ Gene Expression primers and probe set collection and utilized according to manufacturer's instructions. Pooled adipocyte total RNA was serial-diluted in the range of 1.5625-25 ng and used to establish a standard curve; and total RNA for the unknown samples were also diluted in this range. Reactions of quantitative RT-PCR for standards and unknown samples were also performed according to the instructions of Smart Cycler System (Cepheid, Sunnyvale, Calif.) and TaqMan Real Time PCR Core Kit (Applied Biosystems, Branchburg, N.J.). The mRNA quantitation for each sample was normalized using the corresponding 18s quantitation.

FAS Activity: FAS activity was determined spectrophotometrically in adipocyte cytosolic extracts. Adipocytes were homogenized in 250 mmol/L sucrose solution containing 1 mmol/L ethylenediamine-tetraacticacid (EDTA), 1 mmol/L dithiothreitol (DTT), and 100 μmol/L phenylmethylsulfonyl fluoride (PMSF) (pH 7.4). The homogenate was centrifuged at 18,500×g for 1 hr and the infranatant was used for measuring oxidation rate of NADPH.

Intracellular Ca$^{2+}$([Ca$^{2+}$]i): [Ca$^{2+}$]i was measured using a fura-2 dual wavelength fluorescence imaging system. Adipocytes were plated and differentiated in 35 mm dishes with glass coverslips (P35G-0-14-C, MatTek Corporation). Prior to [Ca$^{2+}$]i measurement, cells were preincubated in serum-free medium overnight and rinsed with Hepes Balanced Salt Solution (HBSS) containing the following components (in mM): NaCl 138, CaCl$_2$ 1.8, MgSO$_4$ 0.8, NaH$_2$PO$_4$ 0.9, NaHCO$_3$ 4, glucose 5, glutamine 6, Hepes 20, and bovine serum albumin 1%. Cells were loaded with fura-2 acetoxymethyl ester (AM) (10 μM) in the same buffer for 2 hr at 37° C. in a dark incubator with 5% CO$_2$. To remove extracellular dye, cells were rinsed with HBSS 3 times and then postincubated at room temperature for an additional 1 hr for complete hydrolysis of cytoplasmic fura-2 AM. The dishes with dye-loaded cells were mounted on the stage of Nikon™ S-F fluorescence inverted microscope with a Cohu 4915 CCD camera. Fluorescent images were captured alternatively at excitation wavelength of 340 and 380 nM with an emission wavelength of 520 nM. [Ca$^{2+}$]i was calculated using a standard ratio equation. Each analysis evaluated responses of 8-10 representative whole cells. Images were analyzed with InCytIm2 version 4.62 imaging software (Intracellular Imaging, Cincinnati, Ohio). Images were calibrated using a fura-2 calcium imaging calibration kit (Molecular Probes, Eugene, Oreg.) to create a calibration curve in solution, and cellular calibration was accomplished using digitonin (25 μM) and pH 8.7 Tris-EGTA (100 mM) to measure maximal and minimal [Ca$^{2+}$]i levels.

| | FAS[1] Expression[2] (FAS: 18S) | FAS Activity (nM NADPH/min/ μg DNA) | Triglyceride Content (mg/μg protein) | Intracellular Ca$^{2+}$(nM) |
|---|---|---|---|---|
| Control | 1.79$^a$ ± 0.20 | 57.97$^a$ ± 2.65 | 52.52$^a$ ± 2.42 | 151.3$^a$ ± 8.5 |
| Leucine (0.25 mM) | 0.84$^b$ ± 0.12 | 34.80$^b$ ± 5.14 | 37.98$^b$ ± 0.92 | 75.2$^b$ ± 8.0 |
| Leucine (0.5 mM) | 0.69$^c$ ± 0.11 | 26.47$^{b,c}$ ± 3.59 | 29.73$^{b,c}$ ± 1.35 | 83.7$^b$ ± 11.7 |
| PLP (50 nM) | 1.51$^a$ ± 0.26 | 59.93$^a$ ± 4.11 | 46.62 ± 1.80 | 133.2 ± 9.2 |
| PLP (100 nM) | 1.38$^c$ ± 0.26 | 41.84$^b$ ± 5.57 | 33.98$^b$ ± 1.05 | 96.3$^b$ ± 5.2 |
| Leucine (0.25 mM) + PLP (100 nM) | 0.54$^d$ ± 0.16 | 26.17$^c$ ± 3.33 | 25.12$^c$ ± 0.44 | 59.7$^d$ ± 4.6 |
| Leucine (0.5 mM) + PLP (100 nM) | 0.31$^d$ ± 0.12 | 18.64$^d$ ± 2.89 | 14.46$^d$ ± 0.91 | 64.4$^d$ ± 7.0 |

Non-matching superscripts in each column denote significant differences ($p < 0.01$)
[1]FAS: Fatty Acid Synthase
[2]Expression via real-time RT-PCR normalized to 18S expression Example 4

Interactive Effects of Leucine, Pyridoxal Phosphate (PLP), Metformin, Valine, and Isoleucine on Adipocyte and Myotube Metabolism Measurements Cell Culture: C2C12 and 3T3-L1 preadipocytes (American Type Culture Collection) were plated at a density of 8000 cells/cm$^2$ (10 cm$^2$ dish) and grown in Dulbecco's modified eagle's medium (DMEM) containing 10% fetal bovine serum (FBS), and antibiotics (growth medium) at 37° C. in 5% CO$_2$. Confluent 3T3-L1 preadipocytes were induced to differentiate with a standard differentiation medium consisting of DMEM medium supplemented with 10% FBS, 250 nM dexamethasone, 0.5 mM 3-Isobutyl-1-methylxanthine (IBMX) and 1% penicillin-streptomycin. Preadipocytes were maintained in this differentiation medium for 3 days and subsequently cultured in growth medium. Cultures were re-fed every 2-3 days to allow >90% cells to reach fully differentiation before conducting chemical treatment. For differentiation of C2C12 cells, cells were grown to 100% confluence, transferred to differentiation medium (DMEM with 2% horse serum and 1% penicillin-streptomycin), and fed with fresh differentiation medium every day until myotubes were fully formed (3 days).

Fatty Acid Oxidation: Cellular oxygen consumption was measured using a Seahorse Bioscience XF24 analyzer (Seahorse Bioscience, Billerica, Mass.) in 24-well plates at 37° C., as described by Feige et al (1) with slight modifications. Cells were seeded at 40,000 cells per well, differentiated as described above, treated for 24 hours with the indicated treatments, washed twice with non-buffered carbonate-free pH 7.4 low glucose (2.5 mM) DMEM containing carnitine (0.5 mM), equilibrated with 550 μL of the same media in a non-$CO_2$ incubator for 45 minutes, and then inserted into the instrument for 15 minutes of further equilibration, followed by $O_2$ consumption measurement. Three successive baseline measurements at five-minute intervals were taken prior to injection of palmitate (200 μM final concentration). Four successive 5-minute measurements of $O_2$ consumption were then conducted, followed by 10 minute re-equilibration and another 3-4 5-minute measurements. This measurement pattern was then repeated over a 4-6 hour period. Data for each sample were normalized to the pre-palmitate injection baseline for that sample and expressed as % change from that baseline. Pre-palmitate injection values were 371±14 μmol $O_2$/minute for myotubes and 193±11 μmol $O_2$/minute for adipocytes. The area under of the curve of $O_2$ consumption change from baseline for each sample was then calculated and used for subsequent analysis.

Glucose Utilization: In the absence of a fatty acid source and oxidative metabolism, glycolysis and subsequent lactate production results in extracellular acidification, which was also measured using a Seahorse Bioscience XF24 analyzer. Cells were prepared and equilibrated similar to the methods described above for fatty acid oxidation, with the exclusion of carnitine from the medium. Following instrument equilibration and three baseline measurements, glucose was injected to a final concentration of 10 mM in each well. Measurements were taken as described above utilizing the sensors for extracellular acidification rather than $O_2$ consumption. Insulin (final concentration of 5 nM) was added to some wells as a positive control. Data for each sample were normalized to the pre-glucose injection baseline for that sample and expressed as % change from that baseline. The area under of the curve of extracellular acidification change from baseline for each sample was the calculated and used for subsequent analysis.

Western Blot: The Phospho-AMPKα (Thr172)- and Sirt1 (mouse specific)-antibody was obtained from Cell Signaling (Danvers, Mass.). C2C12 myotubes were treated as indicated in results and the cellular fractions were prepared using standard methods. Protein was measured by BCA kit (Thermo Scientific). For Western blot, 30 μg (for P-AMPK) or 35 μg (for Sirt1) of protein from the cell lysate was resolved on 10% Tris/HCL polyacrylamide gels (Criterion precast gel, Bio-Rad Laboratories, Hercules, Calif.), transferred to PVDF membranes, incubated in blocking buffer (3% BSA in TBS) and then incubated with primary antibody (P-AMPK), washed and incubated with secondary horseradish peroxidase-conjugated antibody. Visualization and chemiluminescent detection was conducted using BioRad ChemiDoc instrumentation and software (Bio-Rad Laboratories, Hercules, Calif.) and band intensity was assessed using Image Lab 4.0 (Bio-Rad Laboratories, Hercules, Calif.), with correction for background and loading controls. P-AMPK was detected at 61-66kDA and Sirt1 was detected at 104-115kDA.

Mitochondrial Biogenesis: Mitochondrial biogenesis was assessed as change in mitochondrial mass, as previously described (2). The mitochondrial probe NAO (Invitrogen, Carlsbad, Calif.) was used to analyze mitochondrial mass by fluorescence (excitation 485 nm and emission 520 nm) and quantitative data was obtained with a fluorescence microplate reader (Synergy HT, BioTek Instruments, Winooski, Vt.). The intensity of fluorescence was expressed as arbitrary units per μg protein and normalized to control values within each assay.

Statistics: Data were analyzed via one-way analysis of variance and least significant difference test was used to separate significantly different group means.

Results

Figure 4:
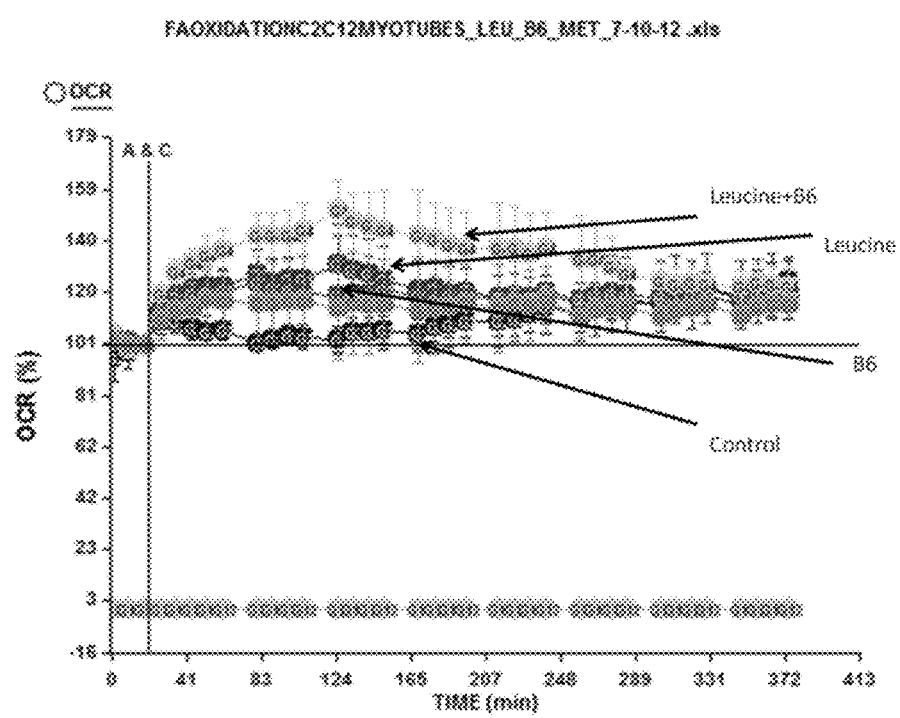
FIG. 4 depicts the effects of leucine with vitamin B6 (pyridoxal phosphate) on fatty acid oxidation in C2C12 myotubes. Fatty acid oxidation was measured as $O_2$ consumption response to palmitate injection and is expressed as % change from pre-injection baseline. The vertical line shows the time of palmitate injection; data points to the left of this line are baseline measurements and those to the right of the line show the $O_2$ consumption response. The combination of leucine and B6 enhanced fatty acid oxidation in muscle cells such as C2C12 myotubes.
Figure 5:
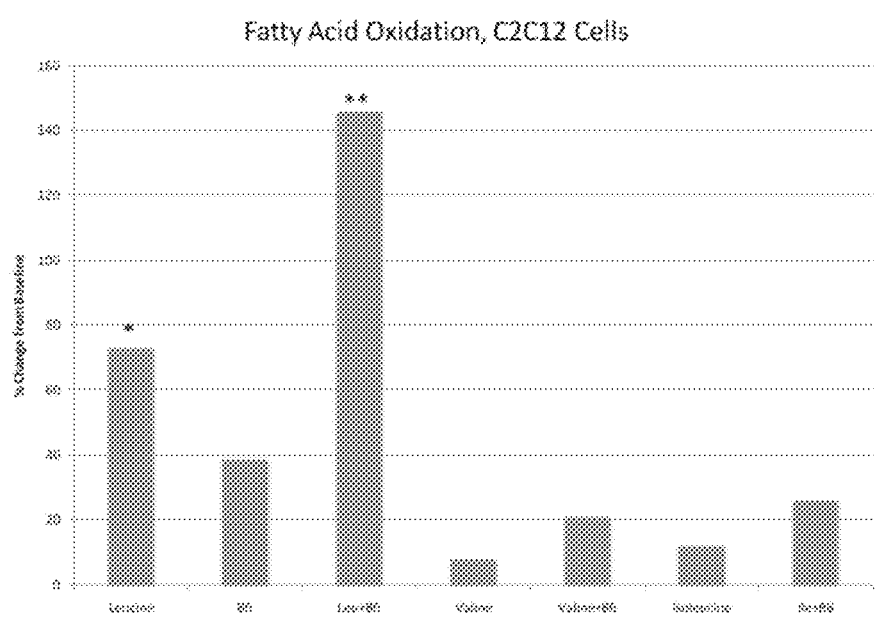
FIG. 5 depicts the interactive effects of leucine, valine or isoleucine with vitamin B6 (pyridoxal phosphate) on fatty acid oxidation in C2C12 myotubes. Data expressed as % change from control value. *p=0.01 vs. control; **p=0.015 vs control or leucine. As the figure shows, treatment with Leucine and B6 yielded an increase in fatty acid oxidation in myotubes that was greater than leucine alone, B6 alone, or the control.
Figure 6:
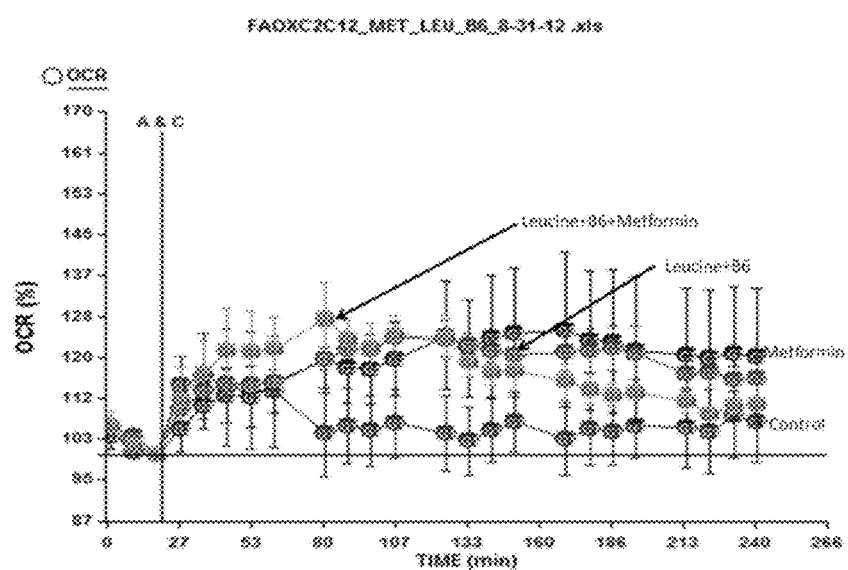
FIG. 6 depicts the interactive effects of leucine with vitamin B6 (pyridoxal phosphate) and metformin on fatty acid oxidation in C2C12 myotubes. Fatty acid oxidation was measured as $O_2$ consumption response to palmitate injection and is expressed as % change from pre-injection baseline. The vertical line shows the time of palmitate injection; data points to the left of this line are baseline measurements and those to the right of the line show the $O_2$ consumption response. The combination of leucine+B6+metformin enhanced fatty acid oxidation in muscle cells such as C2C12 myotubes relative to treatment with leucine+B6, treatment with metformin, or the control.
Figure 7:
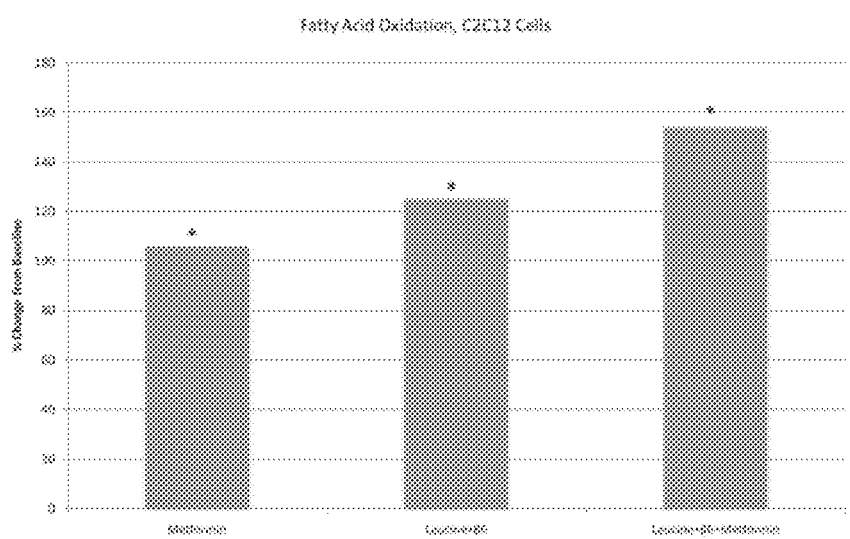
FIG. 7 depicts the interactive effects of leucine with vitamin B6 (pyridoxal phosphate) and metformin on fatty acid oxidation in C2C12 myotubes. Data expressed as % change from control value. *p<0.04. As the figure shows, treatment with Leucine+B6+metformin yielded an increase in fatty acid oxidation in myotubes that was greater than treatment with Leucine+B6 alone, treatment with metformin alone, or the control, but was not greater than the simple additive effect of treatment with Leucine+B6 and Metformin, assuming independent action.
Figure 8:
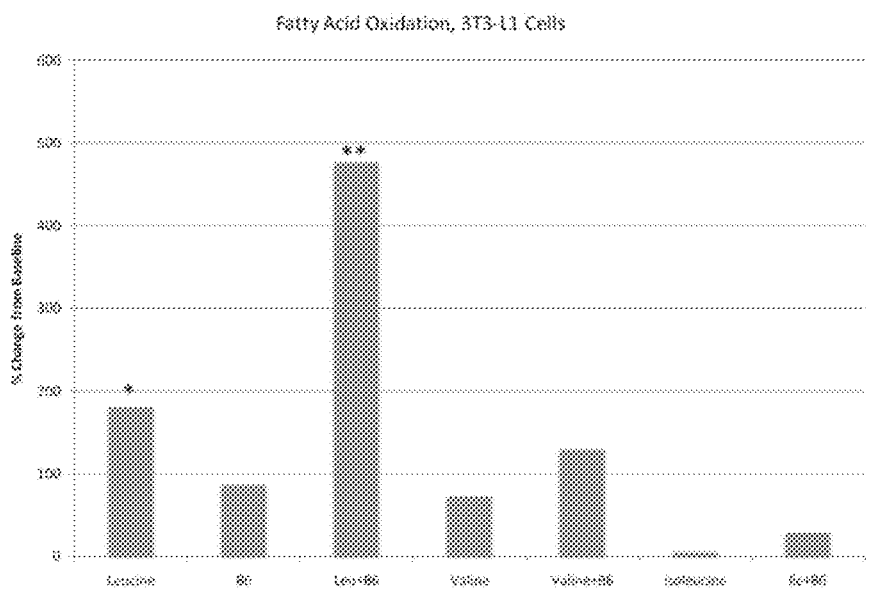
FIG. 8 depicts the interactive effects of leucine or valine with vitamin B6 (pyridoxal phosphate) on fatty acid oxidation in 3T3-L1 adipocytes. Data expressed as % change from control. The data shows that the leucine+B6 combination is more effective in enhancing fatty acid oxidation in adipocyte cells such as 3T3-L1 cells as compared to treatment with leucine or B6 alone at a comparable dosage. Furthermore, the combination of leucine and B6 enhances fatty acid oxidation to an extent greater than the predicted simple additive effect of administering leucine or B6 alone, assuming independent action of leucine and B6.

Fatty Acid Oxidation: FIG. 4 shows the interactive effects of leucine and vitamin B6 on fatty acid oxidation in C2C12 myotubes and significant quantitative data are summarized in FIG. 5. Leucine (0.5 mM) induced a 73% increase in fatty acid oxidation (p=0.01), while B6 (100 nM as pyridoxal phosphate) exerted no significant independent effect. However, combining leucine and B6 resulted in a further increase of 146% (p=0.015 vs. control or leucine). The predicted additive effect would have been 73%, however the increase in fatty acid oxidation to 146% yielded a synergistic effect of a 100% increase over the predicted additive effect. In contrast, substituting either of the other two branched chain amino acids, valine (0.5 mM) or isoleucine (0.5 mM) for leucine, either independently or in combination with B6 resulted in a small change in fatty acid oxidation when compared to control (FIG. 5). The effect of combining valine or isoleucine with B6 increased fatty acid oxidation relative to valine or isoleucine alone, but not to a level that was greater than B6 alone. FIG. 6 shows the interactive effects of leucine, B6 and metformin (100 μM), and quantitative data are summarized in FIG. 7. Similar to as shown in FIG. 4 and FIG. 5, leucine+B6 increased fatty acid oxidation by 125% (p<0.04), and metformin exerted a comparable effect. However, there the effect of combining leucine+B6 with metformin was not greater than the simple additive effect of treating with metformin and with leucine+B6, assuming independent action of metformin and leucine+B6. FIG. 8 shows quantitative effects of leucine and B6 on fatty acid oxidation in 3T3-L1 adipocytes. Leucine treatment increased fatty acid oxidation by 181% (p=0.04), while the leucine-B6 combination increased it by 477% (p=0.008). The effect of treatment with valine alone or B6 alone was around 80-90%, and treatment with valine+B6 yielded an effect of about 125%. Treatment with isoleucine resulted in a small change from baseline, and treatment with isoleucine+B6 resulted in a small increase from baseline to about 30%. The effect of combining B6 with either valine or isoleucine did not result in a change from baseline greater than the sum of the effects, assuming independent action, of treating with B6 alone and treating with either valine or isoleucine alone.

Figure 9:
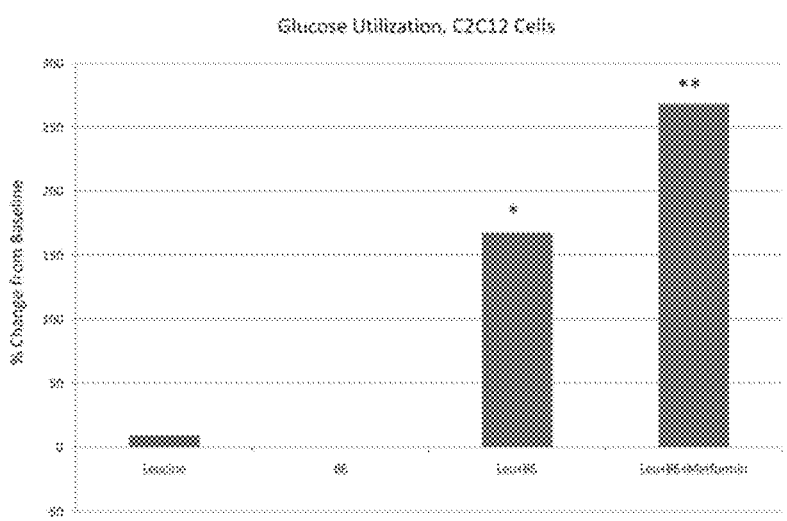
FIG. 9 depicts the interactive effects of leucine with vitamin B6 (pyridoxal phosphate) and metformin on glucose utilization in C2C12 myotubes. Glucose utilization was measured as extracellular acidification response to glucose injection. *p=0.05 vs. control; **p=0.04 vs control or leucine. As the figure shows, treatment of muscle cells such as C2C12 myotubes with leucine+B6+metformin increased glucose utilization relative to treatment with leucine+B6. Treatment with leucine+B6 resulted in an increase in glucose utilization greater than the simple additive effect of treatment with leucine or B6 alone, assuming independent action.
Figure 10:
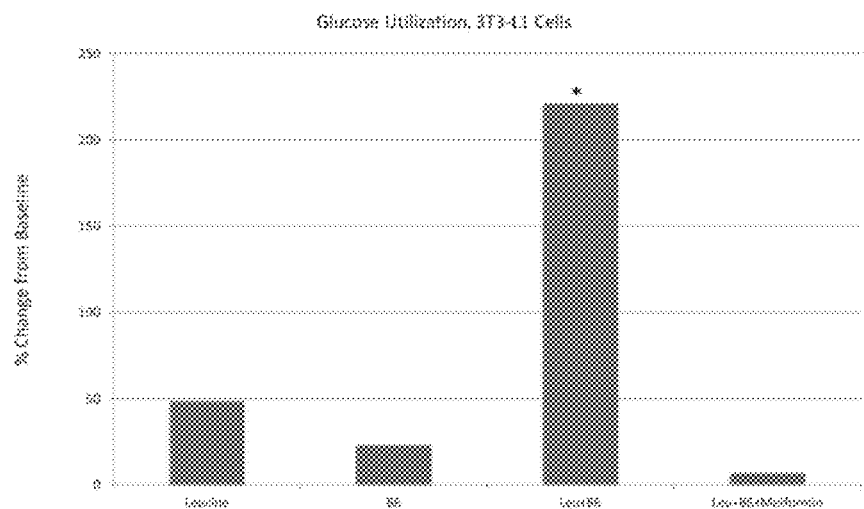
FIG. 10 depicts the interactive effects of leucine with vitamin B6 (pyridoxal phosphate) and metformin on glucose utilization in 3T3-L1 adipocytes. Glucose utilization was measured as extracellular acidification response to glucose injection. *p=0.03. The data shows that treatment of adipocytes, such as 3T3-L1 cells, with leucine+B6 increases glucose utilization to a degree that is greater than the predicted simple additive effect of treatment with leucine and B6 alone.

Glucose Utilization: In contrast to the effects on fatty acid oxidation, leucine exerted no independent significant effect on glucose utilization in either myotubes (FIG. 9) or adipocytes (FIG. 10). Similarly, B6 exerted no independent effect on glucose utilization in either cell type. However, the combination of the two resulted in a 168% increase in glucose utilization in myotubes (p=0.05, FIG. 9) and a 221% increase in adipocytes (p=0.03, FIG. 10). Therefore, the combination composition of B6 and leucine created a synergistic effect that was 168% greater than the predicted additive effect on myotubes and 221% greater than the predicted additive effect on adipocytes. The effects of leucine/B6 were significantly enhanced by metformin in myotubes (FIG. 9), but not in adipocytes (FIG. 10).

Figure 11:
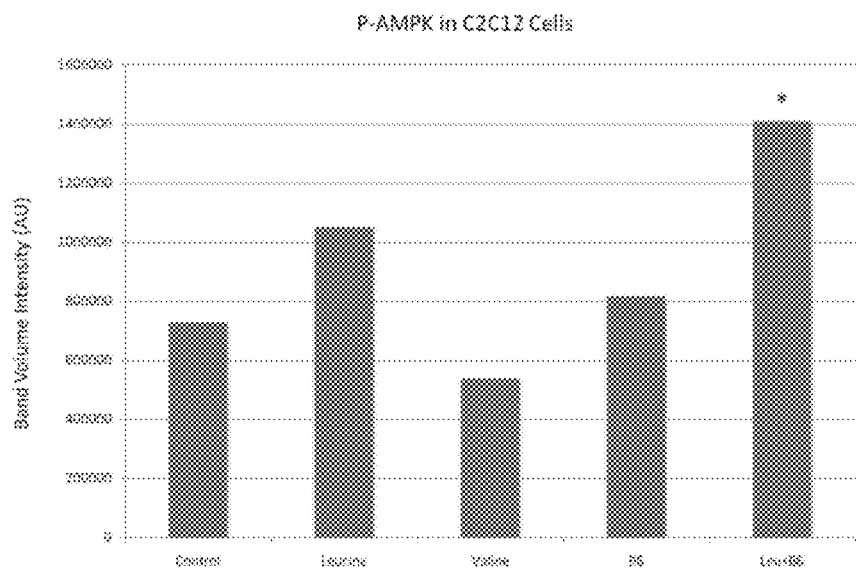
FIG. 11 depicts the interactive effects of leucine or valine with vitamin B6 (pyridoxal phosphate) on Phospho-AMPKα (Thr172) protein expression in C2C12 cellular lysates measured by Western blot. Values are normalized band intensity units. *p=0.0003. As the data shows, treatment of leucine+B6 increased P-AMPK expression to a higher degree than the control or treatment with leucine, valine, or B6 alone.

AMPK: Phosphorylated AMPK (Thr172) was used to assess AMPK activation in myotubes. Neither treatment with leucine, valine, nor B6 alone exerted any significant effect on AMPK activation. However, the combination of leucine and B6 induced a ~two-fold increase in this measure of AMPK activation (p=0.0003, FIG. 11). In contrast, there was no treatment effect on AMPK in adipocytes.

Figure 12:
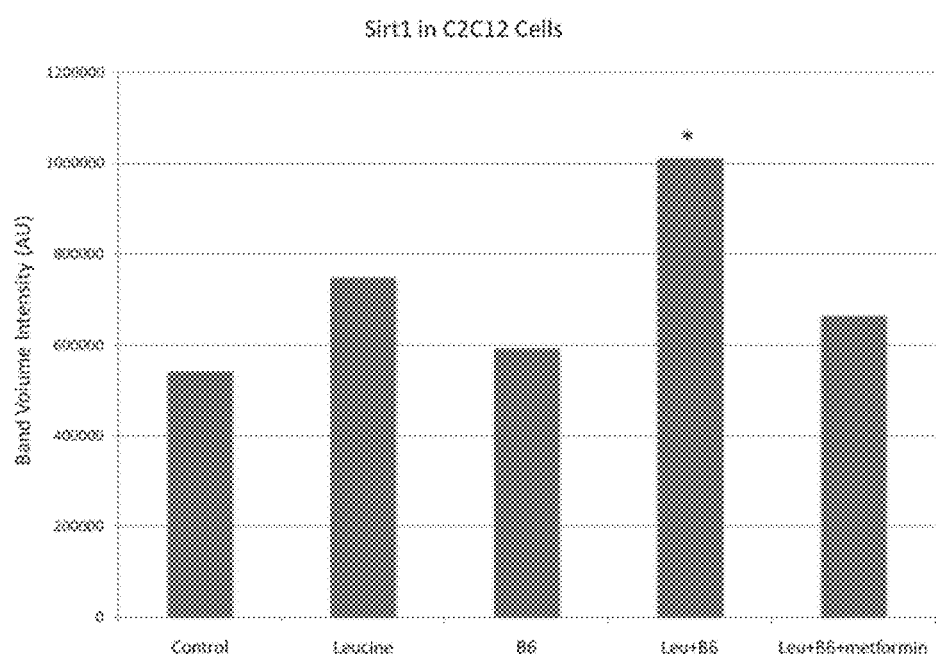
FIG. 12 depicts the interactive effects of leucine with vitamin B6 (pyridoxal phosphate) and metformin on Sirt1 protein expression in C2C12 cellular lysates measured by Western blot. Values are normalized band intensity units. *p=0.002. As the data shows, treatment with leucine or B6 alone did not affect Sirt1 protein expression, but treatment with the combination of leucine and B6 yielded an increase in Sirt1 protein level.

Sirt1: Similar to the AMPK data, Sirt1 protein expression was unaffected by either leucine or B6, but the combination of the two resulted in a ~two-fold increase in Sirt1 protein levels (p=0.002, FIG. 12), but there was no treatment effect of the combination in adipocytes.

Figure 13:
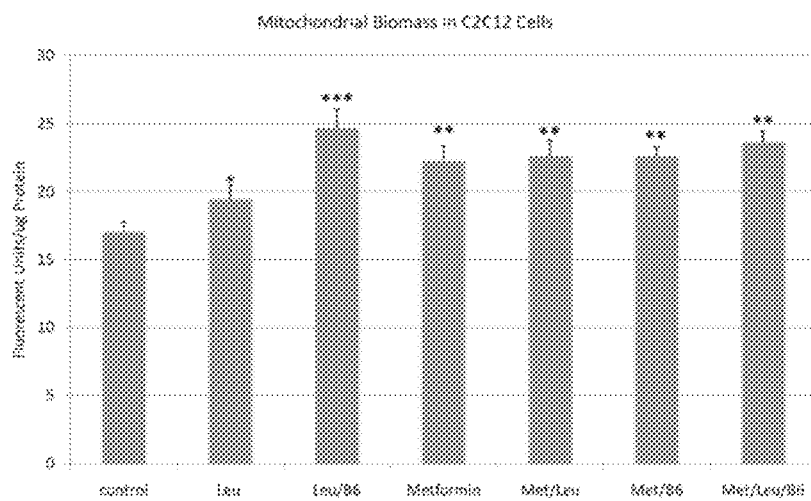
FIG. 13 depicts the interactive effects of leucine with vitamin B6 (pyridoxal phosphate) and metformin on mitochondrial biogenesis, measured as mitochondrial mass, in C2C12 cells. *p=0.04 vs. control; p<0.03 vs. leucine; *p<0.01 vs. all other treatments. As shown in the figure, treatment of myotubes with leucine increased mitochondrial biomass relative to control, and the combination treatment of leucine+B6 increased mitochondrial biomass to an even greater degree.

Mitochondrial Biomass: Leucine stimulated a significant increase in mitochondrial biogenesis (as assessed by mitochondrial biomass) (p=0.04) (about 15%) in myotubes, which was augmented by the addition of B6 (p=0.006; FIG. 13) (about 50%). Metformin exerted an effect similar to leucine, but this effect was not augmented by the addition of leucine, B6 or leucine+B6 (FIG. 13). Other branched chain amino acids (isoleucine, valine) exerted no significant effect on mitochondrial biogenesis, as assessed by a measurement of mitochondrial biomass.

These data demonstrate significant and substantial synergy between leucine and vitamin B6 in stimulating AMPK, Sirt1 and downstream outcomes (fatty acid oxidation, glucose utilization, mitochondrial biomass). These effects are specific to leucine, as they are not recapitulated to the same extent by the other branched chain amino acids. Notably, although leucine exerts an independent effect on fat oxidation, this effect is markedly enhanced by the addition of pyridoxal phosphate, a compound which exerted no independent effects; moreover, there is a clear synergy between leucine and B6 in stimulating glucose utilization, as neither compound exerted a significant independent effect. Also notable that the effect of combining leucine+B6 and metformin lead to increased fatty acid oxidation above either metformin or Leucine+B6 alone, but not to a level greater than the predicted additive effects of leucine+B6 and metformin, assuming that each acted independently.

Example 5

Figure 14:
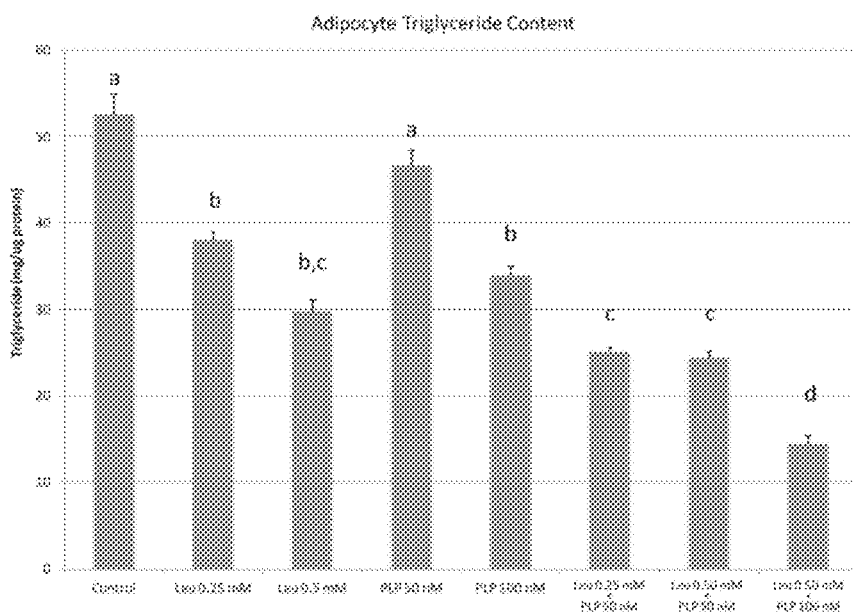
FIG. 14 depicts the interactive effects of B6 (pyridoxal phosphate, PLP) and leucine (Leu) on adipocyte triglyceride content. Cultured 3T3-L1 adipocytes were treated with leucine (0.25 or 0.50 mM), PLP (50 or 100 nM) or combinations thereof. Treatment with 0.5 mM leucine corresponds to a circulating level of the same molarity achieved by administering about 1,125 mg of dietary leucine to a human subject. Treatment with 0.25 mM leucine corresponds to a circulating level of the same molarity achieved by administering about 300 mg of dietary leucine to a human subject. Treatment with 100 nM PLP corresponds to a circulating level of the same molarity achieved by administering about 15 mg of dietary vitamin B6 to a human subject. Treatment with 50 nM PLP corresponds to a circulating level of the same molarity achieved by administering about 7.5 mg of dietary vitamin B6 to a human subject. Reduction in triglyceride accumulation is achieved by 0.5 mM leucine+100 nM PLP, which corresponds to the administration of a dose of about 1,125 mg leucine+15 mg B6 which has a leucine to B6 mass ratio of about 75. Data expressed as mean±SE, and non-matching letters over the bars indicate significant differences between treatments (p<0.01). The data shows a dose-dependent effect of leucine on reducing adipocyte triglyceride content and a dose-dependent effect of B6 on reducing adipocyte triglyceride content. Moreover, the combination of leucine and B6 is more effective in reducing adipocyte triglyceride content as compared to treating with leucine or B6 alone at comparable dosage. The combination of leucine and B6 can have an effect greater than the simple additive effect of leucine or B6, as if they exerted their effects independently. This experiment exemplifies that a combination of leucine and B6 at a dosing mass ratio of at least about 75 or higher and a dose of about 15 mg or higher of B6 is synergistic in reducing adipocyte triglyceride content.

Interactive Effects of Pyridoxal Phosphate (PLP) and Leucine (Leu) on Adipocyte Triglyceride Content Cultured 3T3-L1 adipocytes were treated with leucine (0.25 or 0.50 mM), PLP (50 or 100 nM) or combinations. Treatment with 0.5 mM leucine corresponds to a circulating level of the same molarity achieved by administering about 1,125 mg of dietary leucine to a human subject. Treatment with 0.25 mM leucine corresponds to a circulating level of the same molarity achieved by administering about 300 mg of dietary leucine to a human subject. Treatment with 100 nM PLP corresponds to a circulating level of the same molarity achieved by administering about 15 mg of dietary vitamin B6 to a human subject. Treatment with 50 nM PLP corresponds to a circulating level of the same molarity achieved by administering about 7.5 mg of dietary vitamin B6 to a human subject. As shown in FIG. 14, a reduction in triglyceride content was achieved by 0.5 mM leucine+100 nM PLP, which corresponds to administration of a dose of about 1,125 mg leucine+15 mg B6, which in turn has a leucine to B6 mass ratio of about 75. In comparison, reduction in triglyceride content was not as pronounced when cells were treated with 0.5 mM leucine and 50 nM PLP, which corresponds to administration of 300 mg leucine and 7.5 mg B6, which in turn corresponds to a lower mass ratio of leucine to B6 (about 40).

The triglyceride content was reduced to a lesser extent when the cells were treated with 0.25 mM leucine and 50 nM PLP, suggesting that, where desired, one may enhance triglyceride reduction by increasing the respective molar concentration of leucine and B6 while maintaining the mass ratio (for example 75 or greater).

Data expressed as mean+SE, and non-matching letters over the bars indicate significant differences between treatments (p<0.01). As shown in FIG. 14, the triglyceride reduction can be limited by the dosing level of vitamin B6.

It should be understood from the foregoing that, while particular implementations have been illustrated and described, various modifications can be made thereto and are contemplated herein. It is also not intended that the invention be limited by the specific examples provided within the specification. While the invention has been described with reference to the aforementioned specification, the descriptions and illustrations herein are not meant to be construed in a limiting sense. Furthermore, it shall be understood that all aspects of the invention are not limited to the specific depictions, configurations or relative proportions set forth herein which depend upon a variety of conditions and variables. Various modifications in form and detail of the embodiments of the invention will be apparent to a person skilled in the art. It is therefore contemplated that the invention shall also cover any such modifications, variations and equivalents.

What is claimed is:

1. A composition comprising:
   (a) at least 250 mg of leucine and/or a leucine metabolite; and
   (b) at least about 0.1 mg of vitamin B6;
   wherein the leucine metabolite is selected from the group consisting of keto-isocaproic acid(KIC), alpha-hydroxy-isocaproic acid, and hydroxymethylbutyrate (HMB),
   wherein the mass ratio of component (a) to (b) in said composition is greater than 65,
   wherein the composition is free of the individual amino acids arginine, isoleucine and valine, and
   wherein the composition comprises less than 1% of the individual amino acids alanine, asparagine, aspartic acid, cysteine, glutamic acid, glutamine, glycine, histidine, lysine, methionine, phenylalanine, proline, serine, threonine, tryptophan, and tyrosine.

2. The composition of claim 1, wherein component (a) is present in an amount of at least 1130 mg, and component (b) is present in an amount of at least 12 mg.

3. The composition of claim 1, wherein the composition comprises at least 500 mg of leucine and at least 5 mg of vitamin B6.

4. The composition of claim 1, wherein the composition is formulated as an oral dosage form.

5. The composition of claim 1, wherein the composition is a dietary supplement packaged as a solid food or a semi-solid food.

6. The composition of claim 5, wherein the composition is formulated as a tablet, capsule, or gel capsule.

7. The composition of claim 1, wherein the composition further comprises a food carrier.

8. The composition of claim 1, wherein the composition further comprises one or more of a sweetener, a bulking agent, a stabilizer, an acidulant, and a preservative.

9. The composition of claim 1, wherein the composition has a shelf-life greater than 7 months.

10. The composition of claim 1, wherein the composition further comprises a pharmaceutically active agent or an anti-diabetic agent.

11. The composition of claim 1, wherein the composition further comprises metformin.

12. The composition of claim 1, wherein the mass ratio of component (a) to (b) in the composition is less than 100.

13. The composition of claim 1, wherein the composition is packaged as a liquid composition.

14. The composition of claim 13, wherein the composition comprises at least about 250 mg of the leucine or leucine metabolite per 16 ounces of the liquid composition.

15. A method for increasing energy metabolism in a subject in need thereof comprising administering a composition of claim 1 to the subject to effect an increase in the subject's energy metabolism.

16. A method for enhancing fat oxidation in a subject in need thereof comprising administering the composition of claim 1 at least two times per day to effect an increase in the subject's fat oxidation.

* * * * *